United States Patent
Ford, Jr. et al.

(10) Patent No.: US 10,208,012 B2
(45) Date of Patent: Feb. 19, 2019

(54) COMPOUNDS FOR TREATING INFLAMMATORY AND HYPERPROLIFERATIVE DISEASES

(71) Applicant: Board of Regents, The University of Texas System, Austin, TX (US)

(72) Inventors: Richard J. Ford, Jr., Houston, TX (US); William G. Bornmann, Missouri City, TX (US); Ashutosh Pal, Kirnahar (IN); Lan V. Pham, Missouri City, TX (US); Zhenghong Peng, Missouri City, TX (US); David Maxwell, Pearland, TX (US); Archito Tamayo, Humble, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 318 days.

(21) Appl. No.: 14/774,620

(22) PCT Filed: Mar. 13, 2014

(86) PCT No.: PCT/US2014/026344
§ 371 (c)(1),
(2) Date: Sep. 10, 2015

(87) PCT Pub. No.: WO2014/160339
PCT Pub. Date: Oct. 2, 2014

(65) Prior Publication Data
US 2016/0016931 A1    Jan. 21, 2016

Related U.S. Application Data

(60) Provisional application No. 61/780,508, filed on Mar. 13, 2013.

(51) Int. Cl.
*A61K 9/127* (2006.01)
*C07D 335/02* (2006.01)
(Continued)

(52) U.S. Cl.
CPC ............ *C07D 335/02* (2013.01); *A61K 9/127* (2013.01); *A61K 31/382* (2013.01);
(Continued)

(58) Field of Classification Search
CPC .................................................. A61K 9/127
See application file for complete search history.

(56) References Cited

U.S. PATENT DOCUMENTS 3,979,381 A    9/1976  Rovnyak
5,399,363 A    3/1995  Liversidge et al.
(Continued)

FOREIGN PATENT DOCUMENTS

WO    WO 2012-021692    2/2012

OTHER PUBLICATIONS

STN search report, accessed Sep. 20, 2017.*
(Continued)

*Primary Examiner* — Benjamin J Packard
(74) *Attorney, Agent, or Firm* — Parker Highlander PLLC

(57) ABSTRACT

Compounds are provided that can exhibit anti-cancer and/or anti-inflammatory properties, in some aspects, methods of treating an inflammatory disease or a hyperproliferative disease, such as cancer, with the compounds are provided.

32 Claims, 14 Drawing Sheets

(51) Int. Cl.

| | |
|---|---|
| *A61K 31/382* | (2006.01) |
| *A61K 31/404* | (2006.01) |
| *A61K 31/538* | (2006.01) |
| *A61K 45/06* | (2006.01) |
| *A61N 5/10* | (2006.01) |
| *C07D 209/08* | (2006.01) |
| *C07D 209/12* | (2006.01) |
| *C07D 265/36* | (2006.01) |

(52) U.S. Cl.
CPC .......... *A61K 31/404* (2013.01); *A61K 31/538* (2013.01); *A61K 45/06* (2013.01); *A61N 5/10* (2013.01); *C07D 209/08* (2013.01); *C07D 209/12* (2013.01); *C07D 265/36* (2013.01)

(56) References Cited

U.S. PATENT DOCUMENTS

| | | | |
|---|---|---|---|
| 5,466,468 | A | 11/1995 | Schneider et al. |
| 5,543,158 | A | 8/1996 | Gref et al. |
| 5,580,579 | A | 12/1996 | Ruddy et al. |
| 5,629,001 | A | 5/1997 | Michael et al. |
| 5,641,515 | A | 6/1997 | Ramtoola |
| 5,725,871 | A | 3/1998 | Illum |
| 5,756,353 | A | 5/1998 | Debs |
| 5,780,045 | A | 7/1998 | McQuinn et al. |
| 5,792,451 | A | 8/1998 | Sarubbi et al. |
| 5,804,212 | A | 9/1998 | Illum |
| 6,613,308 | B2 | 9/2003 | Bartus et al. |

OTHER PUBLICATIONS

Costi et al.,"2,6-Bis(3,4,5-trihydroxybenzylydene) derivatives of cyclohexanone: novel potent HIV-1 integrase inhibitors that prevent HIV-1 multiplication in cell-based assays," *Bioorganic & Medicinal Chemistry*, 12(1):199-215, 2004.

Ford et al., "Establishment and characterization of human B-cell lymphoma cell lines using B-cell growth factor," *Blood*, 75(6):1311-1318, 1990.

PCT International Preliminary Report on Patentability issued in International Application No. PCT/US2014/026344, dated Sep. 24, 2015.

PCT International Search Report and Written Opinion issued in International Application No. PCT/US2014/026344, dated Aug. 26, 2014.

Pham et al.,"An epigenetic chromatin remodeling role for NFATc1 in transcriptional regulation of growth and survival genes in diffuse large B-cell lymphomas," *Blood*, 116(19):3899-3906, 2010.

Pham et al., "Chemo-Resistance in Diffuse Large Cell Lymphoma: Novel Drug Combinations Targeting NFAT/NF-Kb Growth/Survival/Chemo-Resistance Signaling Pathways in Validated Novel Experimental Systems," *Blood*, 118:1428, 2011.

\* cited by examiner

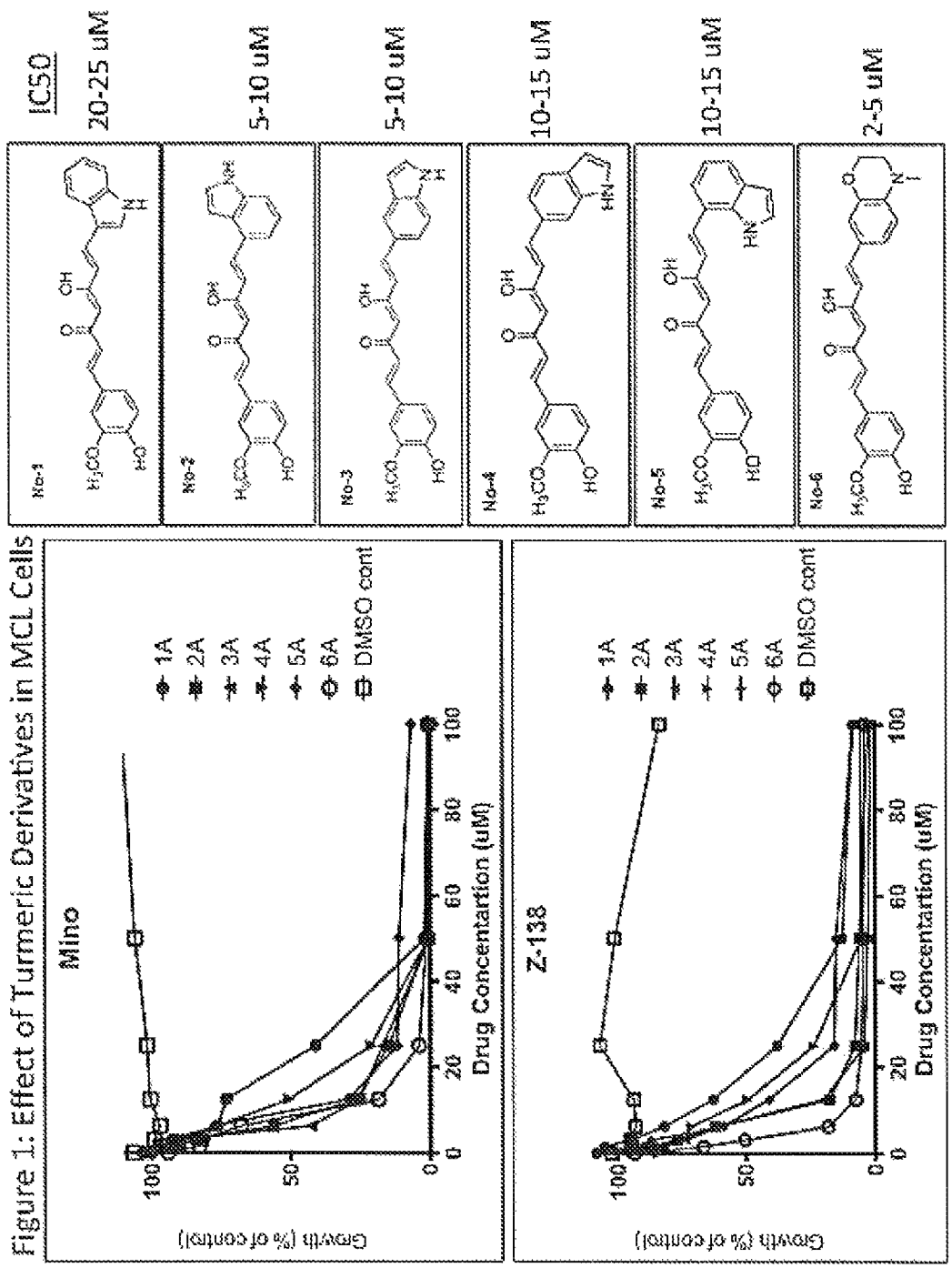

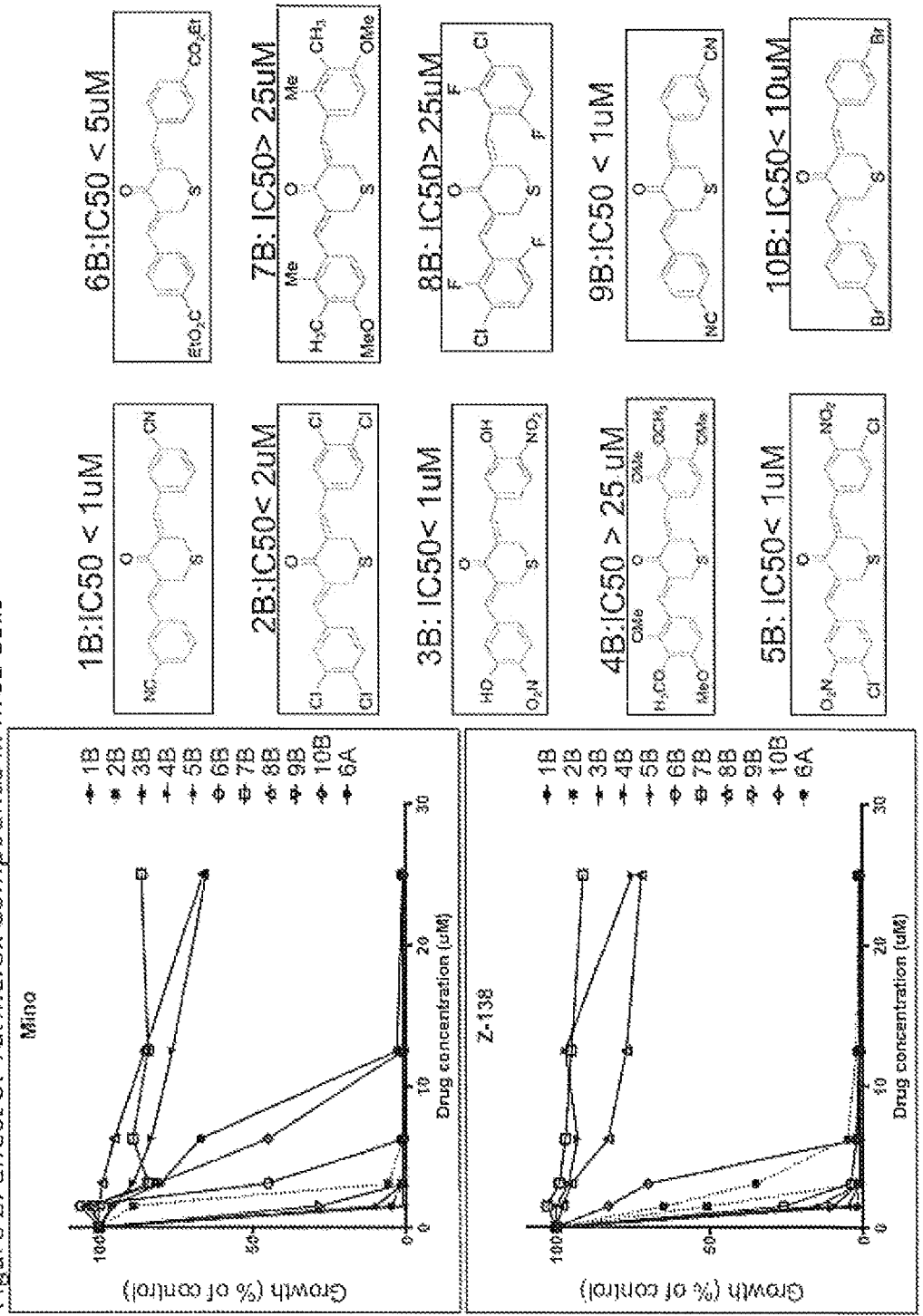
Figure 2: Effect of Turmerax Compounds in MCL Cells

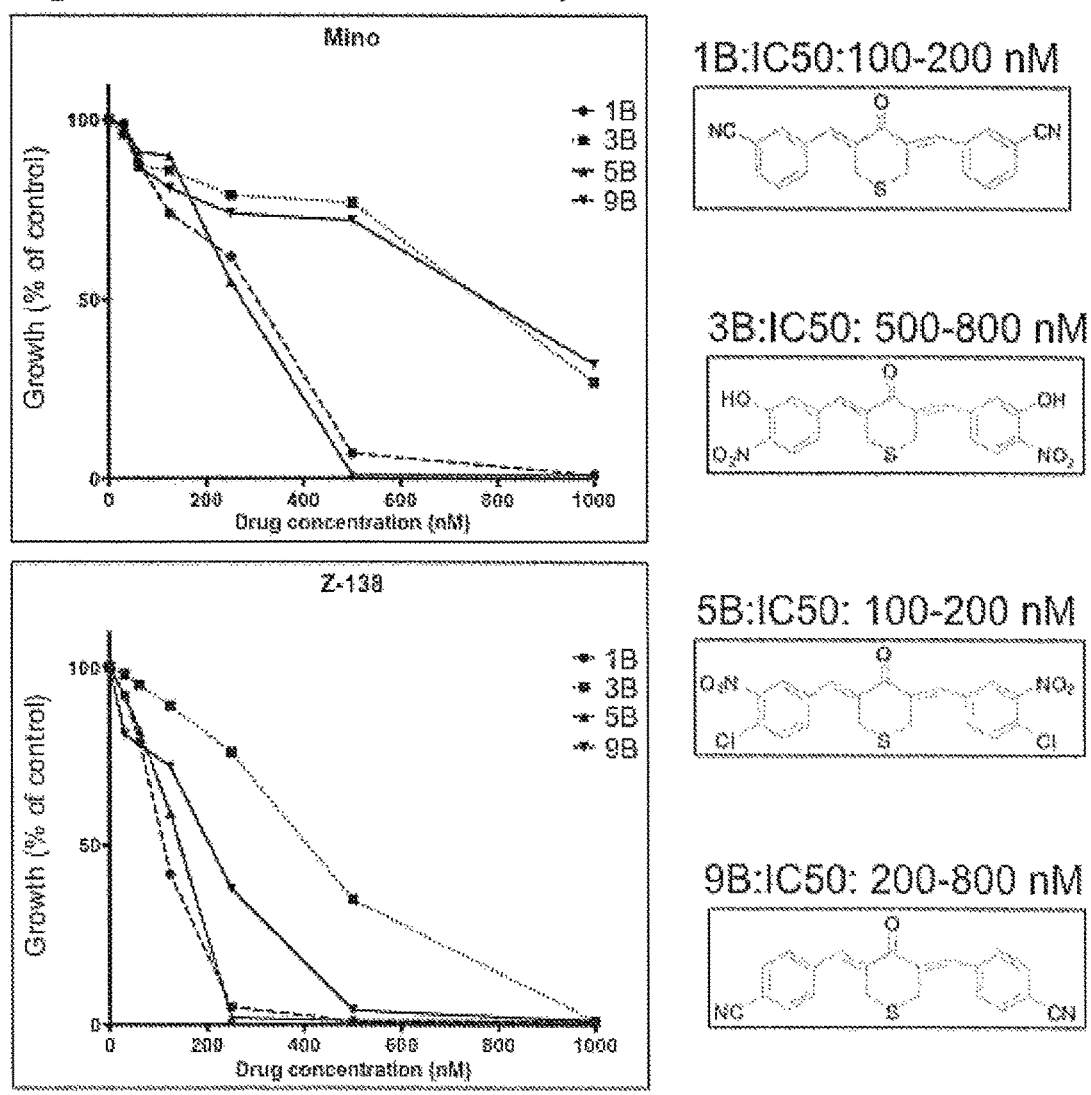

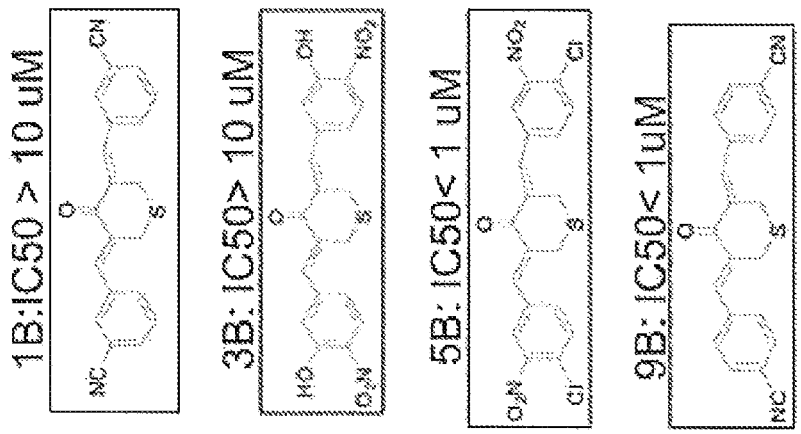
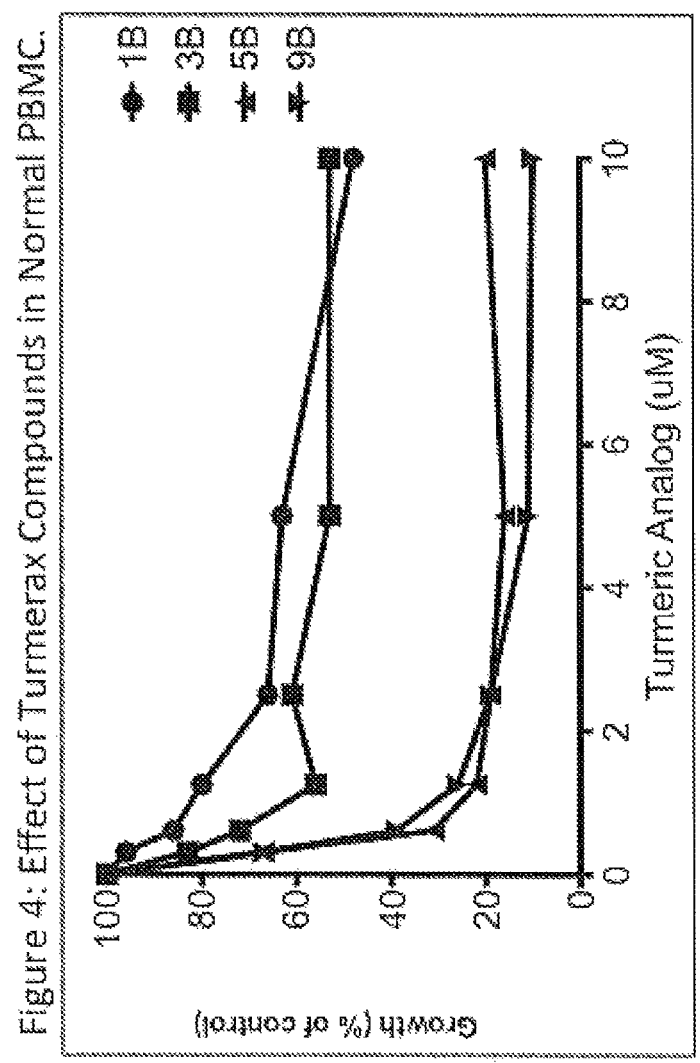
Figure 4: Effect of Turmerax Compounds in Normal PBMC.

Comparison of Turmerax Coumpounds to Curcumin in NHL-B cells

| | | MCL | | | LBCL | | | | FL |
| | | | | | GCB | | ABC | | |
| | Mino | DB | Z-138 | JMP-1 | MS | DB | LR | LP | CJ |
|---|---|---|---|---|---|---|---|---|---|
| Turmerax-1 | 250 nM | 125 nM | 100 nM | 130 nM | 400 nM | 400 nM | 125 nM | 65 nM | 125 nM |
| Turmerax-3 | 250 nM | 125 nM | 125 nM | 250 nM | 450 nM | 450 nM | 150 nM | 100 nM | 125 nM |
| wt-Curcumin | 15 uM | 12 uM | 10 uM | 20 uM | 20 uM | 20 uM | 5 uM | 10 uM | 10 uM |

FIG. 5

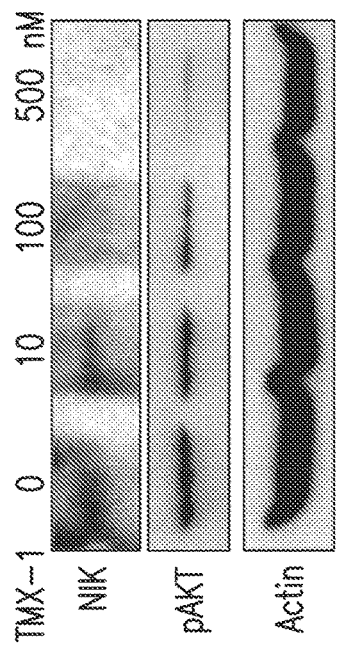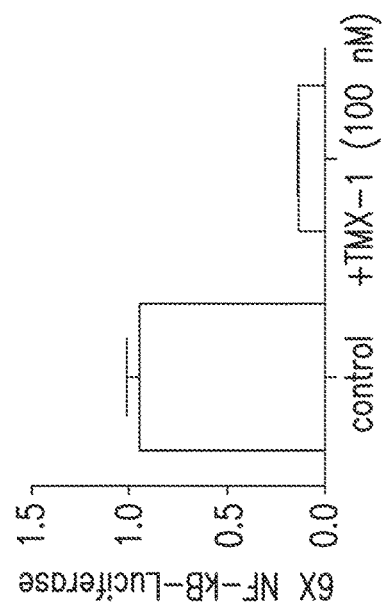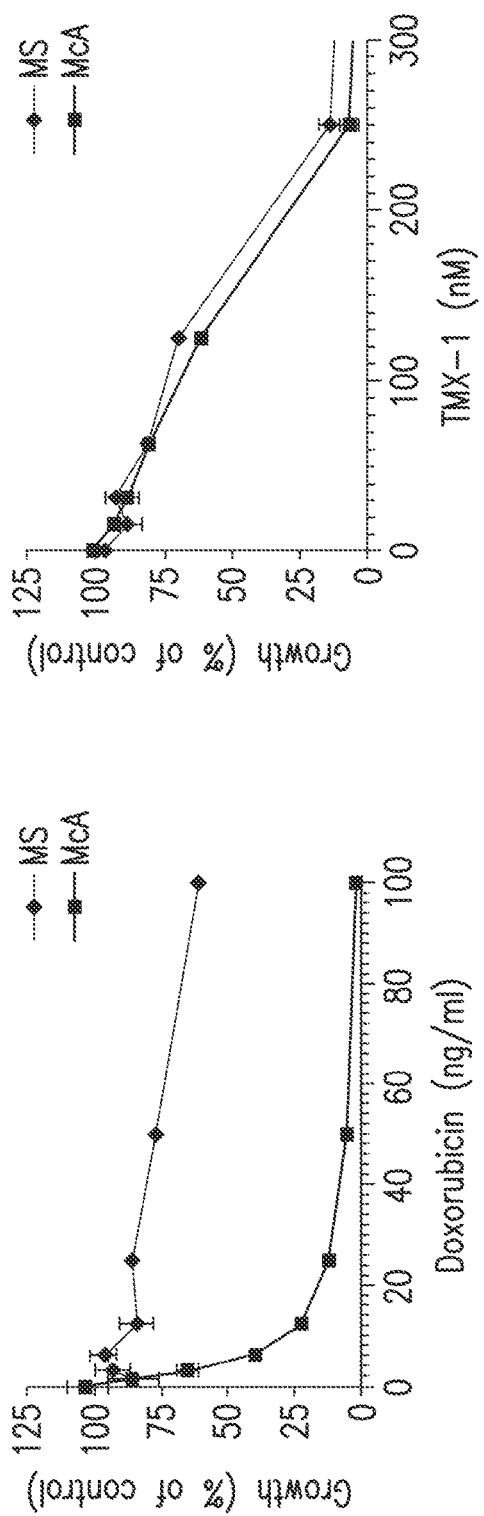
FIG. 7

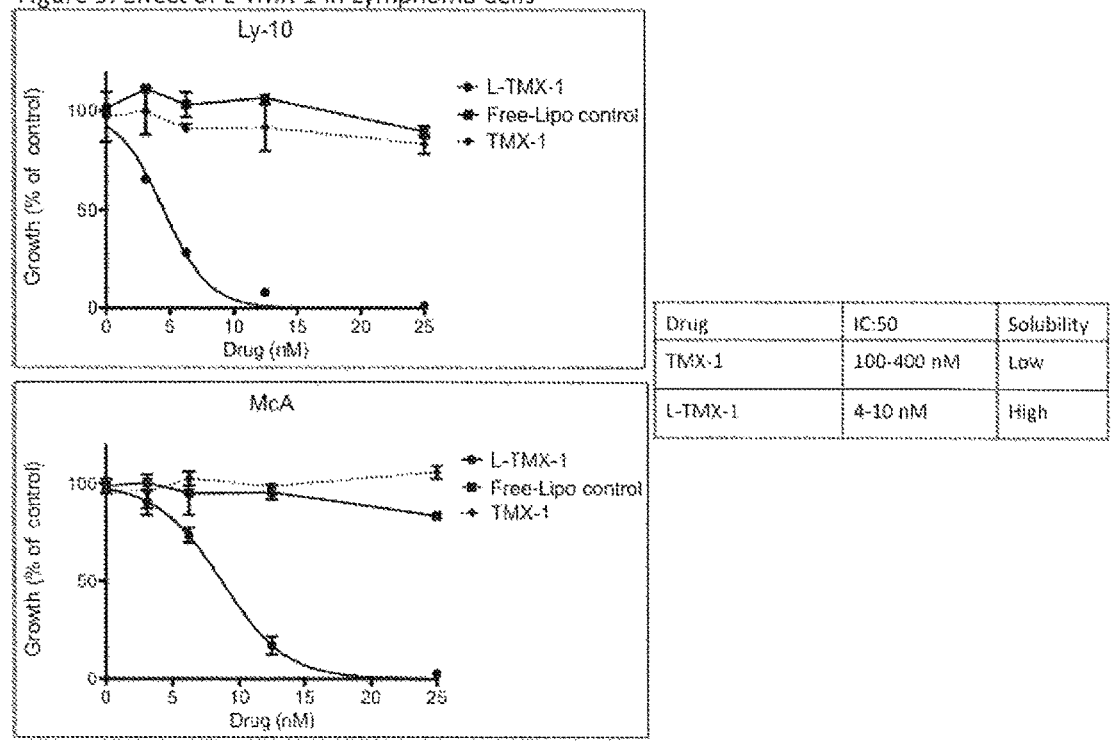

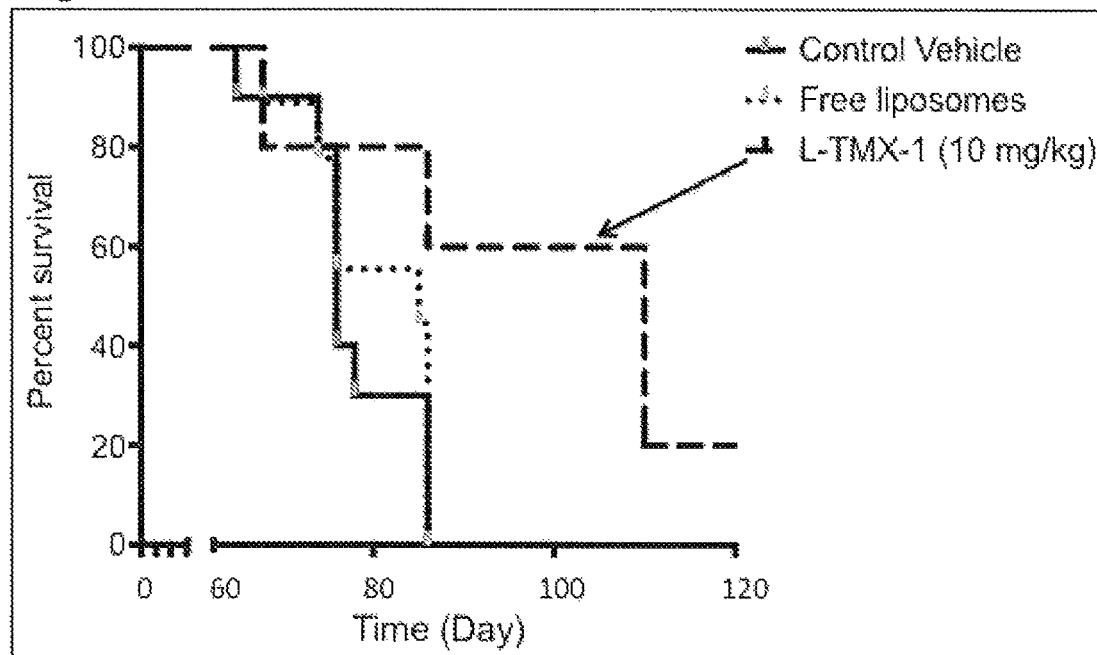

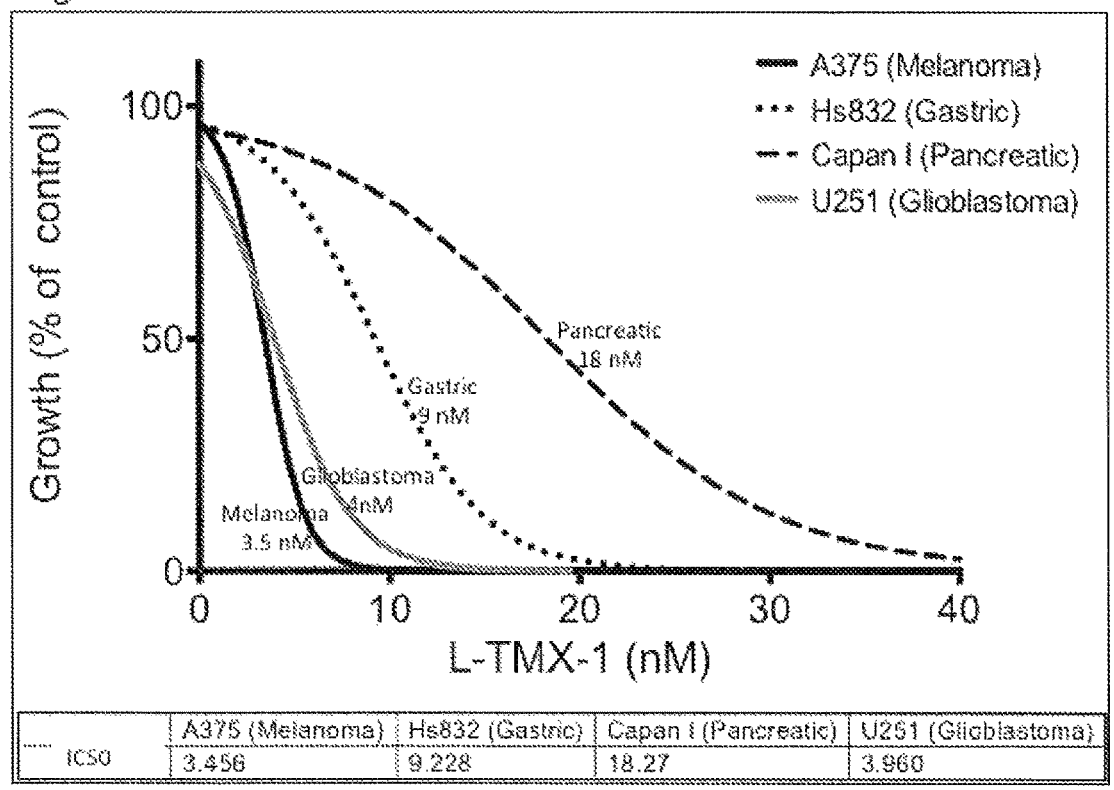

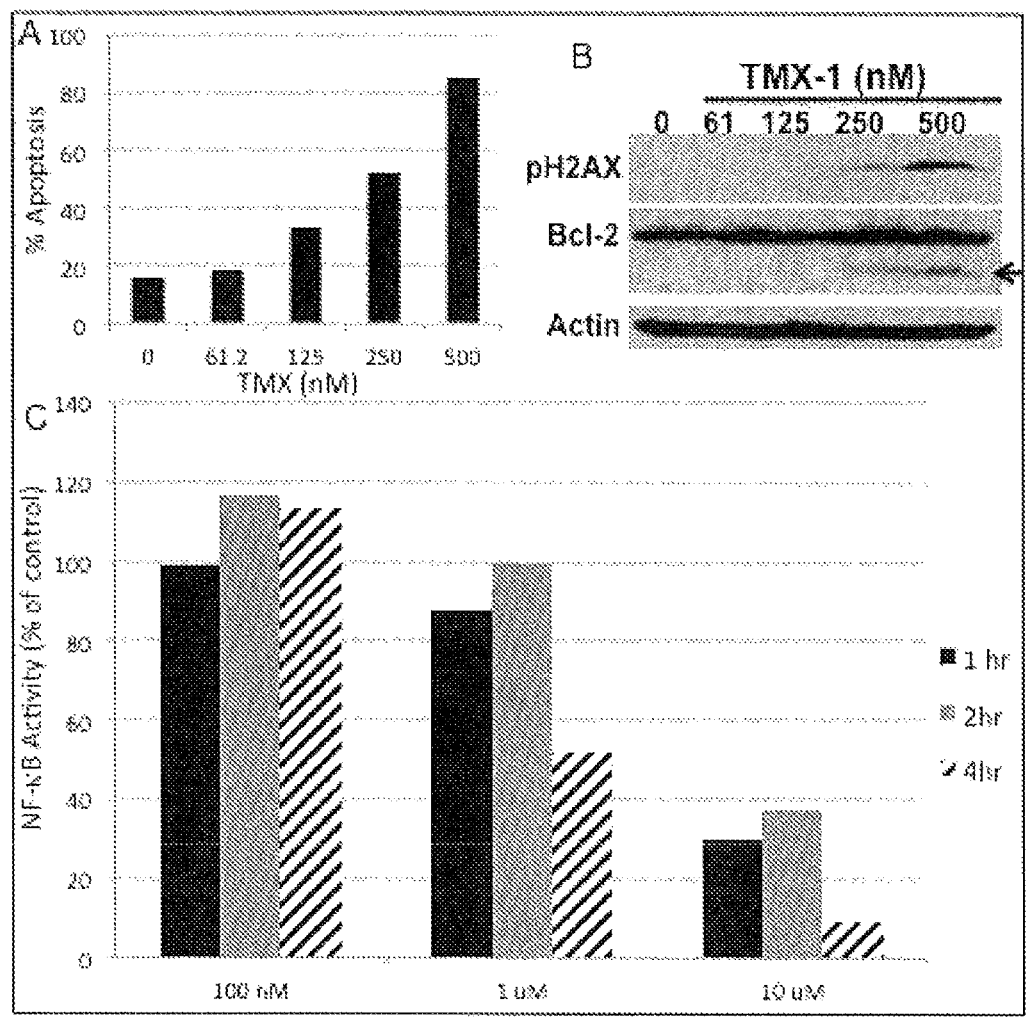
Figs. 12A-C

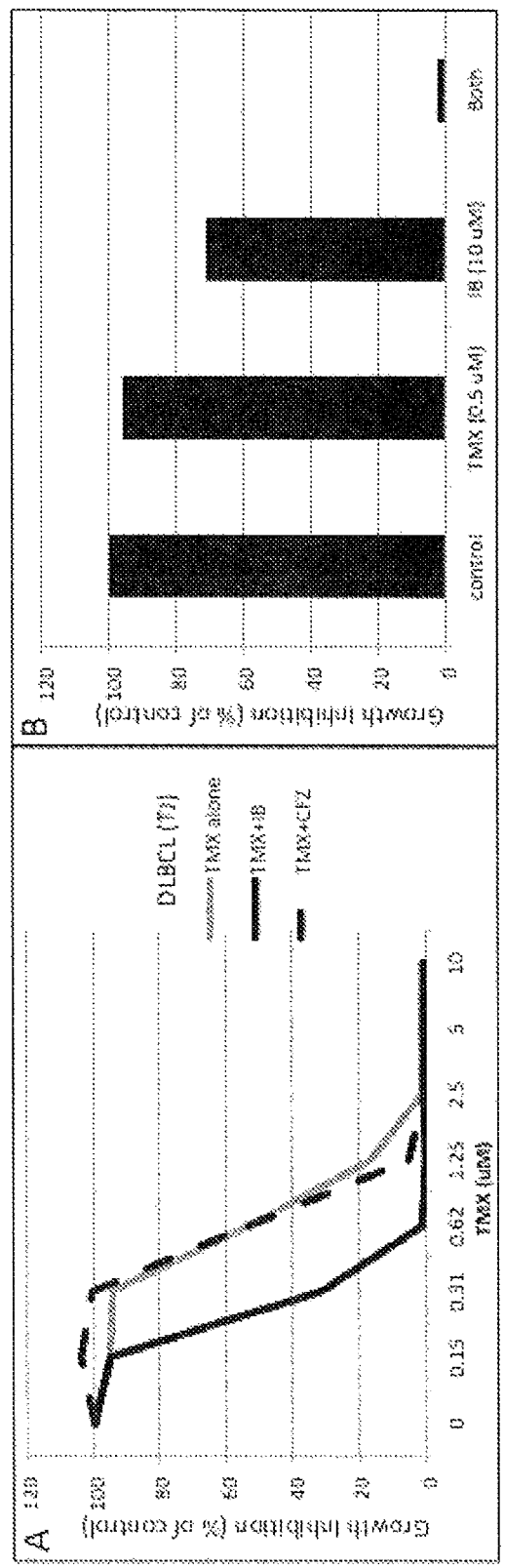
FIGS. 14A-B

COMPOUNDS FOR TREATING INFLAMMATORY AND HYPERPROLIFERATIVE DISEASES

This application is a national phase application under 35 U.S.C. § 371 of International Application No. PCT/US2014/026344, filed Mar. 13, 2014, which claims the benefit of U.S. Provisional Patent Application No. 61/780,508, filed Mar. 13, 2013, the entirety of each of which is incorporated herein by reference.

BACKGROUND OF THE INVENTION

1. Field of the Invention

The present invention relates generally to the field of chemistry, molecular biology, and medicine. More particularly, it concerns compounds that may be used to treat inflammatory diseases or cancer.

2. Description of Related Art

Acquired Chemo-resistance (ACR) is currently the most common cause of treatment failure and early mortality in Diffuse Large B cell Lymphoma (DLBCL), an important lymphoma that currently has a significant unmet need for therapy options. DLBCL, the most common human lymphoma, 1 comprises a genetically and clinically diverse group of aggressive B cell non-Hodgkin lymphomas (NHL-B), among a small group of important human cancers increasing in incidence in the US over the last four decades. 2 NHL-B are the fifth most common cancers in the USA (>62,000 new cases/20,000 deaths) expected in 2011.

Some research has suggested that curcumin may exhibit some anti-cancer effects. Curcumin, (1,7-bis[4-hydroxy-3-methoxyphenyl]-1,6-heptadiene-3,5-dione/diferuloyl methane), the main yellow pigment of the *Curcuma longa* L, has been reported to have antioxidant, antiproliferative and other biological properties. Studies of curcumin in people are still in the relatively early stages. Clearly, there is a need for improved compounds for the treatment of cancer and inflammation.

SUMMARY OF THE INVENTION

The present invention overcomes limitations in the prior art by providing new compounds that may display anti-inflammatory, anti-proliferative, anti-angiogenic, and/or as anti-cancer properties. In some aspects, symmetrical analogs of tetrahydro-3,5-bis[phenylmethylene]-4H-thiopyran-4-one derivatives are provided. The compounds may be synthesized, in various embodiments, using cyclic thio ketone and different substituted aromatic aldehydes, e.g., by treating with concentrated hydrochloric acid in ethanol at about 100° C. In some embodiments, the compounds may exhibit little or no toxicity and/or be used to selectively kill chemoresistant cells. Without wishing to be bound by any theory, the compounds may in some embodiments target multiple growth or survival pathways such as, e.g., NF-κB or AKT. In some aspects and as shown in the below examples, the compounds may display enhanced anti-inflammatory effects, as compared to curcumin.

As shown in the examples below, when encapsulated with nano-liposomes, compounds may be greater than about 1000-fold more effective than curcumin in inhibiting lymphoma cell growth and survival in vitro. Further, compounds were not observed to exhibit little or no toxicity in normal peripheral blood lymphocytes. Without wishing to be bound by any theory, liposomal compositions comprising a compound of the present invention were observed to affect multiple growth and survival signaling pathways, such as NF-kB and AKT, and key cellular regulatory proteins in drug resistance (MDR) in r/r NHL. In vivo these compositions were observed to increase survival time and decrease lymphoma tumor burden in a SCID/MCL xeno-transplant (XT-SCID) mouse model, without evidence of significant host toxicities.

An aspect of the present invention relates to a compound having the structure:

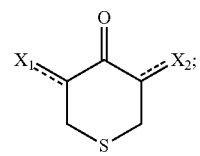

wherein $X_1$ is —H

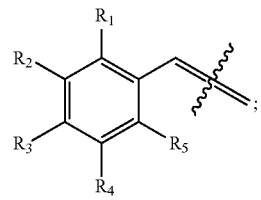

wherein $X_2$ is —H or

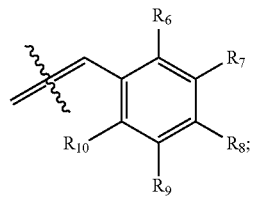

wherein $X_1$ and $X_2$ are not both —H; wherein $R_1$, $R_2$, $R_3$, $R_4$, $R_5$, $R_6$, $R_7$, $R_8$, $R_9$, and $R_{10}$ are each independently —H, —OH, halogen, alkoxy$_{(C1-6)}$, alkylamino$_{(C1-6)}$, dialkylamino$_{(C1-6)}$, acyl$_{(C1-7)}$, alkyl$_{(C1-6)}$, —NH$_2$, —NO$_2$, —CO$_2$H, —CO$_2$-alkyl$_{(C1-6)}$, —CN, —SH, —C(O)NH$_2$, —OC(O)CH$_3$, or —S(O)$_2$NH$_2$; wherein $R_1$-$R_{10}$ are not all hydrogen; or a salt thereof. The compound may have the structure:

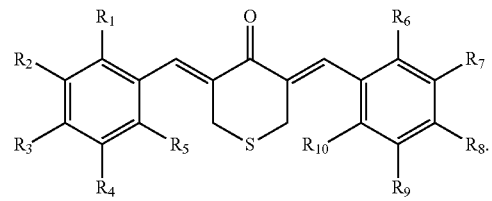

In some embodiments, $R_1$, $R_2$, $R_3$, $R_4$, $R_5$, $R_6$, $R_7$, $R_8$, $R_9$, and $R_{10}$ are each independently —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —CH$_3$, —CH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. In some embodiments, $R_1$, $R_2$, $R_3$, $R_4$, $R_5$, $R_6$, $R_7$, $R_8$, $R_9$, and $R_{10}$ are each independently —H, —OH, —F, —Cl, —Br, —I, —NO$_2$, —CN, —SH, —OCH$_3$, or —OCH$_2$CH$_3$. In some embodiments, $R_1$, $R_2$, $R_3$, $R_4$, $R_5$, $R_6$, $R_7$, $R_8$, $R_9$, and $R_{10}$ are each independently —H, —OH, —F, —Cl, —Br, —I, —NO$_2$, or —CN. In some embodiments, $R_1$, $R_2$, $R_3$, $R_4$, $R_5$, $R_6$, $R_7$, $R_8$, $R_9$, and $R_{10}$ are not alkoxy$_{(C1-6)}$, alkylamino$_{(C1-6)}$, dialkylamino$_{(C1-6)}$, acyl$_{(C1-7)}$, or alkyl$_{(C1-6)}$.

In some embodiments, the compound is further defined as having the structure:

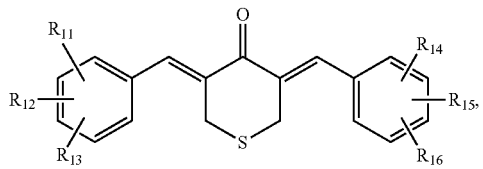

wherein $R_{11}$, $R_{12}$, $R_{13}$, $R_{14}$, $R_{15}$, and $R_{16}$ are each independently —H, —OH, halogen, alkoxy$_{(C1-6)}$, alkylamino$_{(C1-6)}$, dialkylamino$_{(C1-6)}$, acyl$_{(C1-7)}$, alkyl$_{(C1-6)}$, —NH$_2$, —NO$_2$, —CO$_2$H, —CO$_2$CH$_3$, —CN, —SH, —C(O)NH$_2$, —OC(O)CH$_3$, or —S(O)$_2$NH$_2$. In some embodiments, $R_{11}$, $R_{12}$, $R_{13}$, $R_{14}$, $R_{15}$, and $R_{16}$ are each independently —H, —OH, —NO$_2$, —CN, —F, —Cl, —Br, —I, —OCH$_3$, —OCH$_2$CH$_3$, —C(O)OCH$_3$, —C(O)OCH$_2$CH$_3$, —CH$_3$, or —CH$_2$CH$_3$. In some embodiments, the compound is further defined as having the structure:

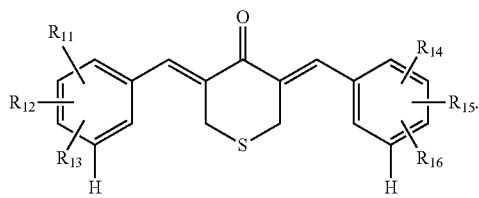

In some embodiments, $R_1$, $R_4$, $R_5$, $R_6$, $R_9$, and $R_{10}$ are —H. In some embodiments, $R_2$ and $R_7$ have the same substituent, or $R_3$ and $R_8$ have the same substituent. In some embodiments, $R_2$ and $R_7$ have the same substituent, and $R_3$ and $R_8$ have the same substituent. In some embodiments, one or more of ($R_1$ and $R_6$), ($R_2$ and $R_7$), ($R_3$ and $R_8$), ($R_4$ and $R_9$), and/or ($R_5$ and $R_{10}$) have the same substituent. In some embodiments, $R_2$, $R_3$, $R_7$, and $R_8$ are each independently —H, —OH, halogen, alkoxy$_{(C1-6)}$, alkylamino$_{(C1-6)}$, dialkylamino$_{(C1-6)}$, acyl$_{(C1-7)}$, alkyl$_{(C1-6)}$, —NH$_2$, —NO$_2$, —CO$_2$H, —CO$_2$-alkyl$_{(C1-6)}$, —CN, —SH, —C(O)NH$_2$, —OC(O)CH$_3$, or —S(O)$_2$NH$_2$. In some embodiments, $R_2$, $R_3$, $R_7$, and $R_8$ are each independently —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —CH$_3$, —CH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. In some embodiments, $R_2$, $R_3$, $R_7$, and $R_8$ are each independently —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. In some embodiments, $R_2$, $R_3$, $R_7$, and $R_8$ are each independently —H, —OH, —Cl, —Br, —NO$_2$, or —CN. In some embodiments, $R_2$ and $R_7$ are —OH, —Cl, —Br, —NO$_2$, or —CN. In some embodiments, $R_3$ and $R_8$ are —OH, —Cl, —Br, —NO$_2$, or —CN.

In some embodiments, the compound has the structure:

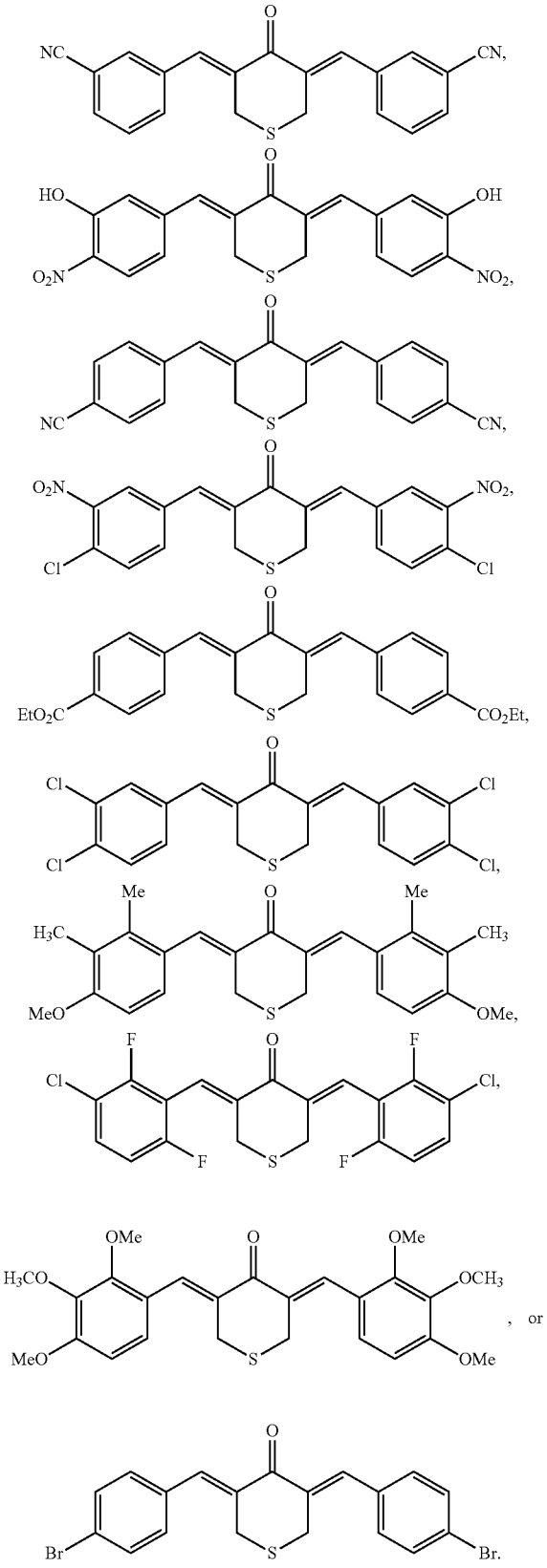

In some embodiments, the compound has the structure:

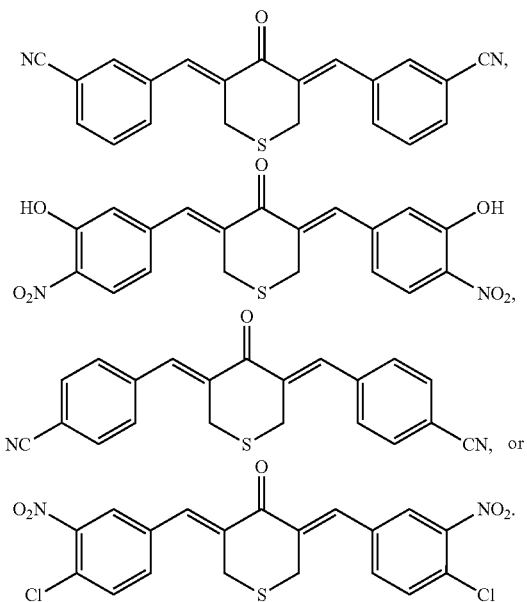

The compound may have the structure:

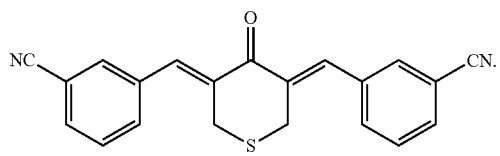 [SMILES: N#Cc1cccc(/C=C2\CSC/C(=C\c3cccc(C#N)c3)C2=O)c1]

In some embodiments, the compound has the structure:

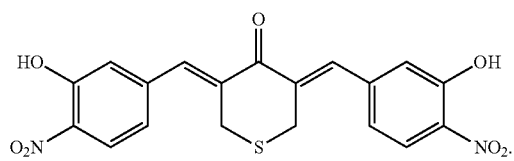 [SMILES: O=C1/C(=C/c2ccc([N+](=O)[O-])c(O)c2)CSC/C1=C\c1ccc([N+](=O)[O-])c(O)c1]

In some embodiments, the compound has the structure:

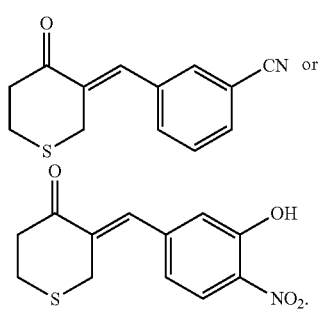

The compound may be comprised in a pharmaceutical preparation or a pharmaceutically acceptable carrier. The pharmaceutical preparation or pharmaceutically acceptable carrier preferably comprises an excipient. The pharmaceutical preparation may be formulated for oral, intravenous, intratumoral, subcutaneous, intraperitoneal, or parenteral administration. The compound may be comprised in a nanoparticle, an exosome, a lipid formulation, or a liposome formulation. The compound may be comprised in a lipid formulation, wherein the lipid is an oil or sesame oil. In some embodiments, the compound is comprised in a liposome formulation, wherein the liposome comprises N-[1-(2,3-Dioleoyloxy)propyl]-N,N,N-trimethylammonium methyl-sulfate (DOTAP), Lipofectamine™, 1,2-dimyristoyl-sn-glycero-3-phosphocholine (DMPC), or 1,2-dimyristoyl-sn-glycero-3-phospho-rac-(1-glycerol) (DMPG). In some embodiments, the liposome comprises 1,2-dimyristoyl-sn-glycero-3-phosphocholine (DMPC) and 1,2-dimyristoyl-sn-glycero-3-phospho-rac-(1-glycerol) (DMPG). In some embodiments, the liposome comprises a ratio of 1,2-dimyristoyl-sn-glycero-3-phosphocholine (DMPC) to 1,2-dimyristoyl-sn-glycero-3-phospho-rac-(1-glycerol) (DMPG) from about 3:1 to about 18:1. In some embodiments, the ratio of 1,2-dimyristoyl-sn-glycero-3-phosphocholine (DMPC) to 1,2-dimyristoyl-sn-glycero-3-phospho-rac-(1-glycerol) is about 6:1 to about 12:1. In some embodiments, the ratio of 1,2-dimyristoyl-sn-glycero-3-phosphocholine (DMPC) to 1,2-dimyristoyl-sn-glycero-3-phospho-rac-(1-glycerol) is about 9:1. In some embodiments, the liposome comprises a ratio of N-[1-(2,3-Dioleoyloxy)propyl]-N,N,N-trimethylammonium methyl-sulfate (DOTAP), Lipofectamine™, 1,2-dimyristoyl-sn-glycero-3-phosphocholine (DMPC), or 1,2-dimyristoyl-sn-glycero-3-phospho-rac-(1-glycerol) (DMPG) to the compound from about 3:1 to about 20:1. In some embodiments, the ratio of N-[1-(2,3-Dioleoyloxy)propyl]-N,N,N-trimethylammonium methyl-sulfate (DOTAP), Lipofectamine™, 1,2-dimyristoyl-sn-glycero-3-phosphocholine (DMPC), or 1,2-dimyristoyl-sn-glycero-3-phospho-rac-(1-glycerol) (DMPG) to the compound is from about 4:1 to about 10:1. In some embodiments, the ratio of N-[1-(2,3-Dioleoyloxy)propyl]-N,N,N-trimethylammonium methyl-sulfate (DOTAP), Lipofectamine™, 1,2-dimyristoyl-sn-glycero-3-phosphocholine (DMPC), or 1,2-dimyristoyl-sn-glycero-3-phospho-rac-(1-glycerol) (DMPG) to the compound is from about 8:1 to about 12:1. In some embodiments, the ratio of N-[1-(2,3-Dioleoyloxy)propyl]-N,N,N-trimethylammonium methyl-sulfate (DOTAP), Lipofectamine™, 1,2-dimyristoyl-sn-glycero-3-phosphocholine (DMPC), or 1,2-dimyristoyl-sn-glycero-3-phospho-rac-(1-glycerol) (DMPG) to the compound is about 10:1. In some embodiments, the liposome may comprise polyethylene glycol (PEG), phosphatidylglycerol (DSPG), dioleoylphosphatidylcholine (DOPC), 1,2-dipalmitoyl-sn-glycero-3-phosphatidylglycerol (DPPG), 1,2-distearoyl-sn-glycero-3-phosphocholine (DSPC), egg lecithin, MPEG-DSPE, Soybean oil, Polysorbate 80, or egg sphingomyelin.

Another aspect of the present invention relates to a compound having the structure:

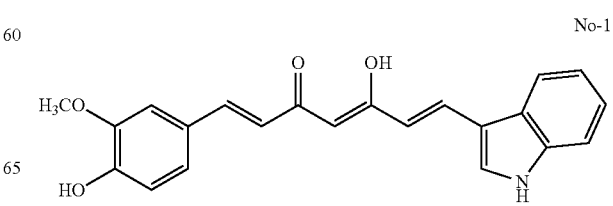

No-1

-continued

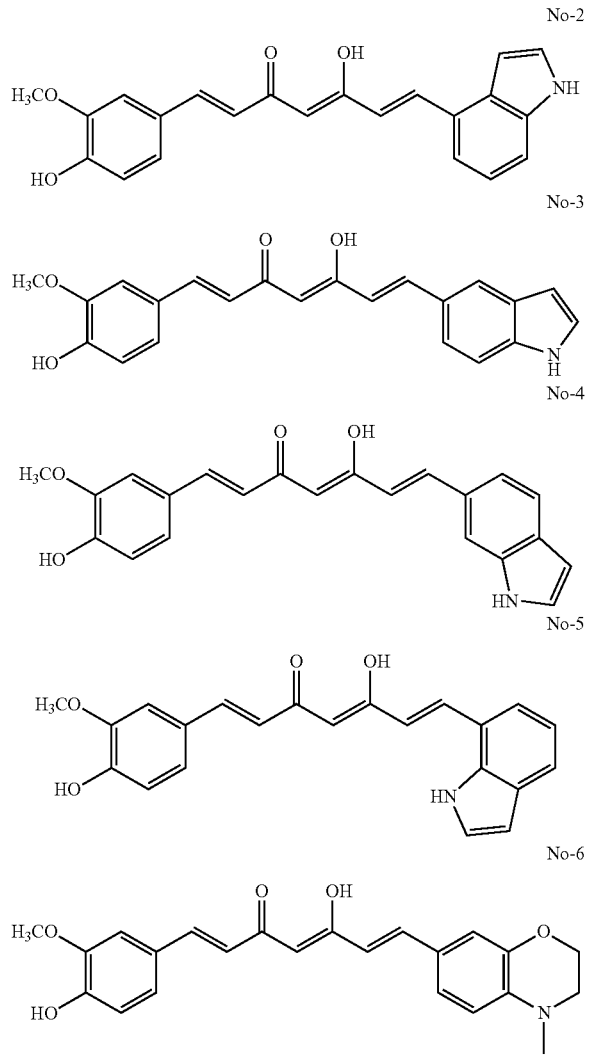

or a salt thereof. The compound may have the structure:

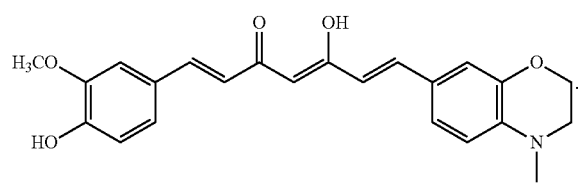 [SMILES: COc1cc(/C=C/C(=O)/C=C(O)/C=C/c2ccc3c(c2)OCCN3C)ccc1O]

Yet another aspect of the present invention relates to a method of treating, preventing, or reducing the likelihood of a cancer in a subject comprising administering a pharmaceutically effective amount of a compound the present invention to treat the cancer. The cancer may be a breast cancer, a cervical cancer, an ovarian cancer, a prostate cancer, a kidney cancer, a bladder cancer, a lung cancer, a liver cancer, a pancreatic cancer, an esophageal cancer, a laryngeal cancer, a stomach cancer, a colon cancer, a thyroid cancer, a melanoma, a gastric cancer, a brain cancer, a glioma, a glioblastoma multiforme, a skin cancer, breast cancer, a brain cancer, a head/neck cancer, a colon cancer, squamous cell carcinoma, an endometrial cancer, an oral carcinoma, a glioblastoma, Hodgkin's lymphoma, acute lymphoblastic leukemia, acute myelogenous leukemia, chronic lymphocytic leukemia, burkitts lymphoma, mantle cell lymphoma, myelodsplastic syndrome, multiple myeloma, diffuse large B-cell lymphoma, a malt lymphoma, a T cell lymphoma, a T cell leukemia, or a non-Hodgkin lymphoma. In some embodiments, the cancer is a T cell lymphoma, a T cell leukemia, a brain cancer, a non-Hodgkin lymphoma, or a glioblastoma multiforme. The subject may be a human, mouse, rat, primate, cat, or dog. The compound may be administered to the subject in an amount of about 1-50 mg/kg. The administration may be oral, intravenous, intratumoral, intraperitoneal, subcutaneous, or intramuscular. The method may further comprise administering a second anti-cancer therapy to the subject such as, e.g., a chemotherapy, and immunotherapy, a radiotherapy, a gene therapy, or a surgery. In some embodiments, the second anti-cancer therapy comprises or consists of administering an inhibitor of Bruton's tyrosine kinase (btk) (e.g., carfilzomib, CFZ) or a proteasome inhibitor (e.g., ibrutinib) to the subject.

Another aspect of the present invention relates to a method of treating inflammation in a subject comprising administering a pharmaceutically effective amount of a compound of the present invention to treat the inflammation. The inflammation may result from pancreatitis, or an autoimmune disease. In some embodiments, the inflammation results from an autoimmune disease, wherein the autoimmune disease is Lupus erythematosis, Sjogren's disease, or rheumatoid arthritis (RA). The subject may be a human, mouse, rat, primate, cat, or dog. The compound may be administered to the subject in an amount of about 1-50 mg/kg. The administration may be oral, intravenous, intratumoral, intraperitoneal, subcutaneous, or intramuscular. The method may further comprise administering a second anti-inflammatory therapy to the subject.

Yet another aspect of the present invention relates to a method of treating an angiogenic disease or reducing angiogenesis in a subject comprising administering a pharmaceutically effective amount of a compound of the present invention to reduce angiogenesis. The subject may have an angiogenic disease such as, e.g., an eye disease, a cancer, or a diabetic retinopathy. The administration may be oral, intravenous, intratumoral, intraperitoneal, subcutaneous, intramuscular, via injection into the eye, topical application onto the surface of the eye, or via intravitreal injection.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Effect of Tumeric Derivatives in MCL cells. Six TMX analogs were screened in two mantle cell lymphoma cell lines (Mino and Z-138). These assays were performed by treating cells with increasing doses of TMX (0-25 µM) and analyzed by thymidine incorporation (proliferation assay).

FIG. 2. Effect of Turmerax Compounds in MCLs. 10 additional TMX analogs derived from compound #6 (from FIG. 1) were screened in two mantle cell lymphoma cell lines (Mino and Z-138). These assays were performed by treating cells with increasing doses of TMX (0-25 µM) and analyzed by thymidine incorporation (proliferation assay).

FIG. 3. Effect of Turmerax Compounds in MCLs. Four compounds from FIG. 2 were selected to analyze at concentrations below 1 µM for cell growth inhibition in vitro.

FIG. 4. Effect of Turmerax compounds in normal peripheral blood mononuclear cells (PBMC). Turmeric analogues (1, 3, 5, and 9) were evaluate for cytoxicity in normal human peripheral blood mononuclear cells (PBMC) by thymidine incorporation assays.

FIG. 5. Comparison of Turmerax compounds 1 and 2 with natural curcumin in different NHL subtypes. MCL cells (Mino, DB, Z-138, and JMP-1), DLBCL cells (MS, DB, LR, and LP) and Follicular lymphoma cells (CJ) were treated with increasing doses of Turmerax-1, Turmerax-2, or Curcumin for 96 hrs and analyzed by thymidine incorporation assays. $IC_{50}$ values were obtained.

FIG. 7. TMX-1 Targets NF-kB and Key Signaling Pathways in DLBCL to Overcome Chemoresistance. Top left, DLBCL cells (MS) were transfect with the 6×-NF-kB-luciferase expression vector for 24 hrs. Transfected cells were treated with PBS (control) or Lipo-TMX-1 (100 nM) for 4 hrs. Cell lysates were used to analyzed for luciferase activity that was normalized with b-gal activity. Top right, TMX-1 inhibited NIK and pAKT in NHL-B cells. MS cells were treated with increasing doses of Lipo-TMX-1 (0-500 nM) for 24 hrs. NIK and pAKT protein expressions were determined by Western blotting. Bottom, Doxorubicin resistant cells are sensitive to TMX-1. MS cells are resistant to Dox, but are sensitive to TMX-1. McA DLBCL cells are sensitive to both doxorubicin and TMX-1.

FIG. 9. Effect of Liposomal encapsulated Turmerax in DLBCL cells. Proliferation assays of DLBCL cell lines LY-10 and McA responding to liposomal turmerax-1 (Lipo-TMX-1) vs free liposomes. The solubility of Lipo-TMX-1 is higher than TMX-1 or curcumin.

FIG. 10. Anti-tumor Effect of Liposomes-encapsulated Turmerax in MCL-SCID mouse model Mice were injected with MCL cells (Mino) and began treatment on day 7. Mice received a vehicle control (PBS), Free liposomes, or Lipo-TMX-1 (10 mg/kg) in 100 ul volume by IP injection (n=9). Survival curves after treatments were created. Mice treated with Lipo-TMX-1 significantly survive longer than control vehicle treated mice (p value=0.0072). Two Lipo-TMX-1-treated mice still remain alive beyond 200 days.

FIG. 11. Effect of TMX-1 in NF-kB-Associated Cancers. Representative cancer cell lines for melanoma, gastric, pancreatic, and glioma were used to analyzed for cell growth inhibition activity of TMX-1 using MTT assays.

FIGS. 12A-C. TMX-1 induces apoptosis in lymphoma cells. (FIG. 12A) A representative lymphoma cell line (LY10) was treated with TMX-1 in a dose-dependent manner for 24 hrs. Apoptosis was determined by Annexin V assays. (FIG. 12B) TMX-1 activates phospho-H2AX (DNA damage marker) and induces bcl-2 cleaving in lymphoma cells. (FIG. 12C) A representative DLBCL cell line (MS) was transfected with a NF-kB-luciferase reporter for 24 hrs. Cells were treated with TMX-1 as indicated.

(FIG. 13A) 24 representative DLBCL cell lines were treated with TMX-1 in dose-dependent manner and analyzed by thymidine incorporation assays for cell growth inhibition. (FIG. 13B) Effect of TMX-1 in doxorubicin highly sensitive and highly resistant DLBCL cell lines (Pham et al., 2011).

FIGS. 14A-B. A representative DLBCL cell line (TJ) was treated with TMX-1 in a dose-dependent manner alone or in combination with Ibrutinib (IB) and carfilzomib (CFZ) and cell proliferation assays were analyzed.

DESCRIPTION OF ILLUSTRATIVE EMBODIMENTS

1. Chemical Group Definitions

Figure 6:
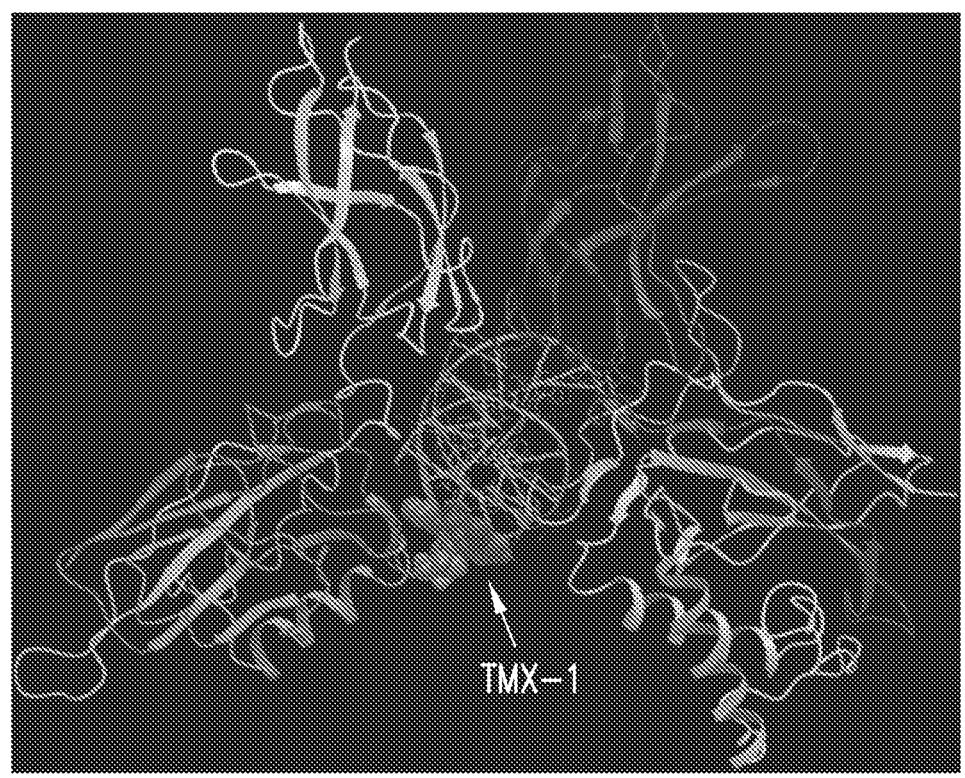
FIG. 6. Interaction of TMX-1 and NF-κB. A proposed structional representation of covalenty bound TMX-1 in NF-κB crystal structure. The p50/p56 heterodimer of NF-κB is shown as ribbons. Residue Cys38 with the TMX-1 molecule covalenty attached is shown as a gray CPK model. Based on this model, there is clear overlap of TMX-1 with DNA.

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "- - - -" represents an optional bond, which if present is either single or double. The symbol "⩴" represents a single bond or a double bond. Thus, for example, the structure

includes the structures

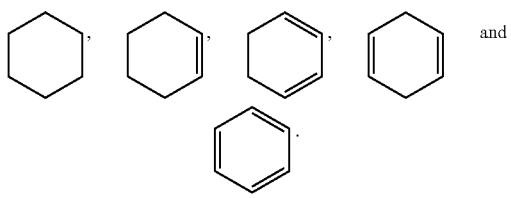

As will be understood by a person of skill in the art, no one such ring atom forms part of more than one double bond. The symbol " ~~~ ", when drawn perpendicularly across a bond indicates a point of attachment of the group. It is noted that the point of attachment is typically only identified in this manner for larger groups in order to assist the reader in rapidly and unambiguously identifying a point of attachment. The symbol " ▬▬ " means a single bond where the group attached to the thick end of the wedge is "out of the page." The symbol " ⋯⋯ " means a single bond where the group attached to the thick end of the wedge is "into the page". The symbol " ~~~ " means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

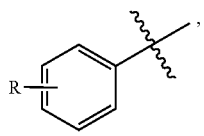

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

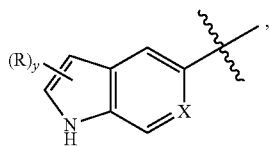

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). Where the term "aliphatic" is used without the "substituted" modifier, then only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

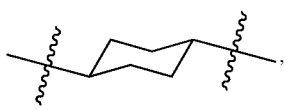 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups. —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

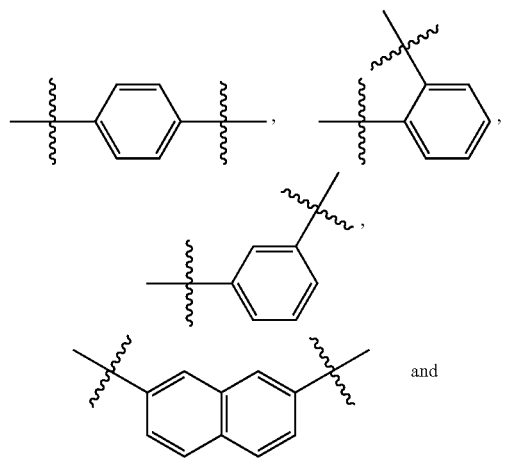

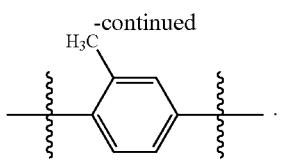

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

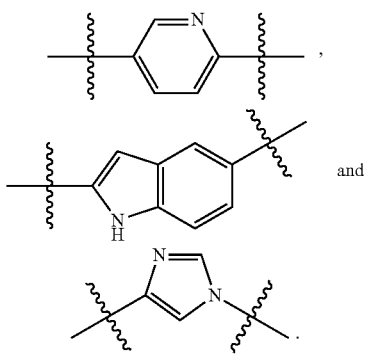

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. As used herein, the term does not preclude the presence of one or more double bonds in the ring or ring system, provided that the resulting groups remains non-aromatic. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH %, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$", "IC:50", or "IC50" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta. 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, -[—$CH_2CH_2$—]$_n$-, the repeat unit is —$CH_2CH_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and p-iodoethoxycarbonyl).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds of the Invention

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

In some embodiments, compounds may be synthesized according to the following synthetic method. A general procedure for the synthesis of symmetric turmeric analogs is shown below in Scheme 1. The bis(benzylidine) derivatives may be achieved or synthesized by a condensation between one equivalent of thioketone and two equivalents of aldehyde employing concentration hydrochloric acid in ethanol at about 100° C. The products may be crystallized out with the progress of the reaction and the product may be filtered, washed with ethanol, and dried.

Scheme 1. General procedure for the synthesis of synthetetrahydro-3,5-bis[phenylmethylene]-4H-thiopyran-4-one derivaties

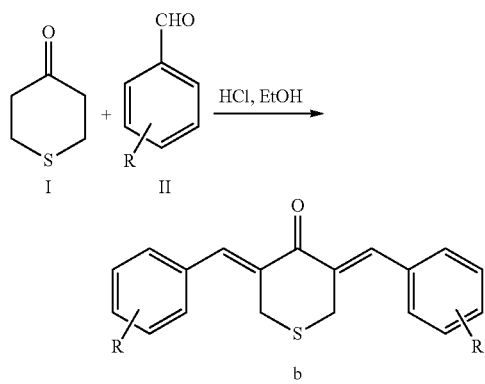

R = different substitutions, e.g., as indicated in the claims and summary sections.

III. Process Scale-Up

The above methods can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2012), which is incorporated by reference herein.

IV. Treatment of Cancer or Inflammation

In various aspects, a compound of the present invention may be used to treat inflammation or a hyperproliferative disease such as cancer. Inflammation may result from an inflammatory disease such as, e.g., atherosclerosis, rheumatoid arthritis, pancreatitis, cancer, or trauma. The inflammatory disease may be acute or chronic.

In some embodiments, a pharmaceutically effective amount of a compound of the present invention may be administered to a subject to treat a hyperproliferative disease or inflammatory disease. The subject may be a mammal such as, e.g., a human, primate, mouse, rat, dog, cat, ape, or monkey. Cancer cells that may be treated with cell targeting constructs according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma wisquamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

V. Pharmaceutical Compositions

Pharmaceutical compositions of the present invention comprise an effective amount of one or more compounds of the present invention, e.g., a compound of the present invention, or additional agent dissolved or dispersed in a pharmaceutically acceptable carrier. In some embodiments, a compound of the present invention may be conjugated with a pharmaceutically acceptable carrier such as a nanoparticle or biotin. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one compound or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, conjugates, antioxidants, preservatives (e.g., antibacterial agents, antifungal agents), isotonic agents, absorption delaying agents, salts, preservatives, drugs, drug stabilizers, gels, polymers, nanoparticles, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18$^h$ Ed. Mack Printing Company, 1990, pp. 1289-1329, incorporated herein by reference). Except insofar as any conventional carrier is incompatible with the active ingredient, its use in the pharmaceutical compositions is contemplated.

The compound of the present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The compound of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, polymers, nanoparticles, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a compound of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the compound of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with or conjugated with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. In some embodiments, a range of about 1-100 mg/kg, about 1-75 mg/kg, about 5-50 mg/kg, about 1-50 mg/kg, or about 1-25 mg/kg may be administered to a subject, such as a human patient.

B. Alimentary Compositions and Formulations

In preferred embodiments of the present invention, the compound of the present invention is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

C. Parenteral Compositions and Formulations

In further embodiments, a compound of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,613,308, 5,466,468, 5,543,158; 5,641, 515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

D. Miscellaneous Pharmaceutical Compositions and Formulations

In other preferred embodiments of the invention, the active compound may be formulated for administration via various miscellaneous routes, for example, topical or transdermal administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

II. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Turmerax compounds are newly synthesized chemical agents with some similarities to a component of the ginger spice turmeric, and its yellow pigment curcumin. Over novel turmerax analogs (tetrahydro-3,5-bis[phenylmethylene]-4H-thiopyran-4-one derivatives) have been designed and synthesized using cyclic thioketone and different substituted aromatic aldehydes by treating with concentrated hydrochloric acid in ethanol at 100° C. These compounds were tested for anti-inflammatory and anti-proliferative activity. Overall the results indicate that modification could enhance the anti-proliferative effects as well as the anti-inflammatory effects of related compounds such as curcumin. The study establishes a structure-activity relationship that will be used to guide further design of newer and more potent analogs of natural product turmeric components.

Chemistry

The general procedure for the synthesis of symmetric turmeric analogs is shown in Scheme 1. The bis(benzylidine) derivatives were achieved by a condensation between one equivalent of thioketone and two equivalents of aldehyde employing concentration hydrochloric acid in ethanol at 100° C. The products were crystallized out with the progress of the reaction and it was filtered, washed with ethanol and dried.

Scheme 1. General procedure for the synthesis ofsynthetetrahydro-3,5-bis[phenylmethylene]-4H-thiopyran-4-one derivaties

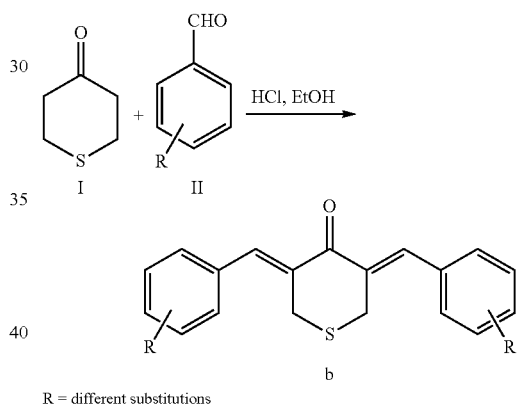

R = different substitutions

Preparation of 3,5-bis[(3-cyanophenyl)methylene]-tetrahydrothiopyran-4-one (1b) Turmerax 1

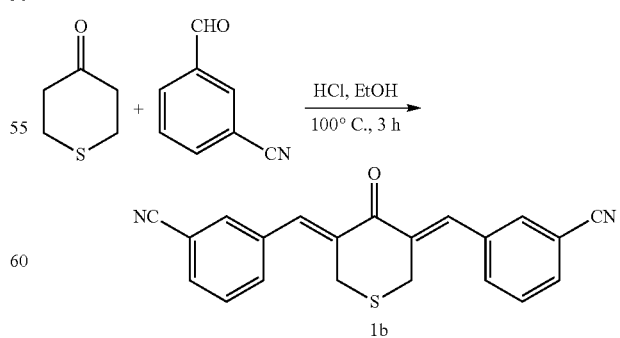

A solution of cyclic tetrahydrothiopyran-4-one 1 (580 mg, 5 mmol), and the 3-cyanobenzaldehyde (1.31 g, 10 mmol), was dissolved in 10 mL ethanol. To this solution 0.6 mL concentrated hydrochloric acid was added and the mixture was refluxed at 100° C. for 3 h. After the solution was cooled, the yellow product was filtered, washed with ethanol and dried in vacuum to give 1.3 g (80%) of product (1b). mp 203-205° C.; IR 1577.8, 1664.24, 2225.9; $^1$H NMR (CDCl$_3$) δ 7.72 (s, 2H), 7.67 (m, 4H), 7.62 (d, J=7.8 Hz, 2H), 7.57 (t, J=8.4 Hz, 2H), 3.86 (s, 4H); $^{13}$C NMR δ 188.0, 134.9, 134.5, 133.3, 133.0, 131.5, 130.7, 129.1, 29.9; MS (C$_{21}$H$_{24}$N$_2$OS) calcd. 342.082 found (M−H) 341.2.

Preparation of 3,5-bis[(3,4-dichlorophenyl)methylene]-tetrahydrothiopyran-4-one (2b) Turmerax 2

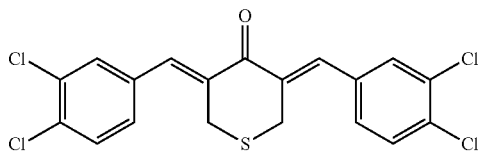 [SMILES: O=C1/C(=C/c2ccc(Cl)c(Cl)c2)CSC/C1=C\c1ccc(Cl)c(Cl)c1]

$^1$H NMR (CDCl$_3$) δ 7.65 (s, 2H), 7.50 (d, J=7.8 Hz, 2H), 7.48 (d, J=2.4 Hz, 2H), 7.22 (dd, J=1.8, 10.2 Hz, 2H), 3.86 (s, 4H); $^{13}$C NMR δ 188.0, 163.2, 125.5, 134.5, 134.0, 133.0, 132.3, 129.7, 118.2, 113.2, 29.9; mp 155-157° C.; IR 1598.92, 1655.74; MS (C$_{19}$H$_{12}$Cl$_4$OS) calcd. 427.936 found (M−H) 428.8.

Preparation of 3,5-bis[(3-hydroxy-4-nitrophenyl)methylene]-tetrahydrothiopyran-4-one (3b) Turmerax 3

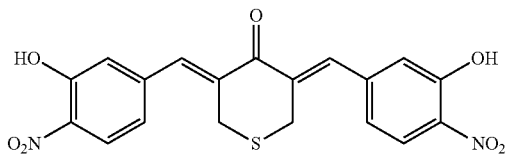 [SMILES: O=C1/C(=C/c2ccc([N+](=O)[O-])c(O)c2)CSC/C1=C\c1ccc([N+](=O)[O-])c(O)c1]

$^1$H NMR (CDCl$_3$) δ 10.65 (s, 2H), 8.19 (d, J=8.4 Hz, 2H), 7.68 (s, 2H), 7.18 (d, J=1.8, Hz, 2H), 7.09 (dd, J=1.2, 8.4 Hz, 2H), 3.90 (s, 4H); $^{13}$C NMR δ 187.8, 154.9, 144.3, 136.7, 134.2, 133.2, 125.5, 121.5, 120.7, 30.0; mp 164-167° C.; IR 1579.02, 1617.82, 1665.34; MS (C$_{19}$H$_{14}$N$_2$O$_7$S) calcd. 414.052 found (M−H) 413.3.

Preparation of 3,5-bis[(2,3,4-trimethoxyphenyl)methylene]-tetrahydrothiopyran-4-one (4b) Turmerax 4

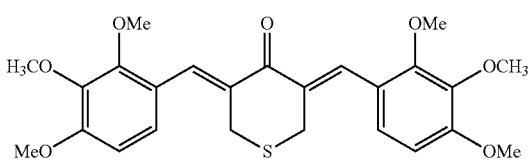 [SMILES: COc1ccc(/C=C2\CSC/C(=C\c3ccc(OC)c(OC)c3OC)C2=O)c(OC)c1OC]

$^1$H NMR (CDCl$_3$) δ 7.85 (s, 2H), 6.99 (d, J=9.0 Hz, 2H), 6.69 (d, J=8.4 Hz, 2H), 3.90 (s, 4H), 3.89 (s, 6H), 3.88 (s, 6H), 3.82 (s, 6H); $^{13}$C NMR δ 188.9, 154.7, 153.3, 142.5, 133.7, 132.4, 125.2, 122.3, 107.0, 61.5, 61.0, 56.1, 30.4; mp 181-183° C.; IR 1586.38, 1665.26; MS (C$_{25}$H$_{28}$O$_7$S) calcd. 472.156 found (M+H) 473.2.

Preparation of 3,5-bis[(3-nitro-4-chlorophenyl)methylene]-tetrahydrothiopyran-4-one (5b) Turmerax 5

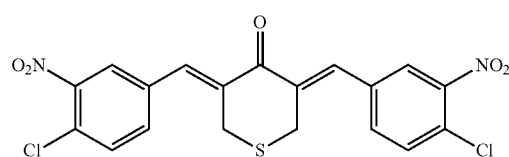 [SMILES: O=C1/C(=C/c2ccc(Cl)c([N+](=O)[O-])c2)CSC/C1=C\c1ccc(Cl)c([N+](=O)[O-])c1]

$^1$H NMR (CDCl$_3$) δ 7.89 (d, J=1.8 Hz, 2H), 7.69 (s, 2H), 7.63 (d, J=8.4 Hz, 2H), 7.52 (dd, J=1.8, 8.4 Hz, 4H), 3.92 (s, 4H); $^{13}$C NMR δ 188.5, 135.1, 134.8, 133.3, 132.4, 127.6, 126.4, 29.9; mp 201-203° C.; IR 1528.01, 1580.76, 1662.79; MS (C$_{19}$H$_{12}$Cl$_2$N$_2$O$_5$S) calcd. 449.984 found (M−H) 449.0.

Preparation of 3,5-bis[(4-ethoxycarbonylphenyl)methylene]-tetrahydrothiopyran-4-one (6b) Turmerax 6

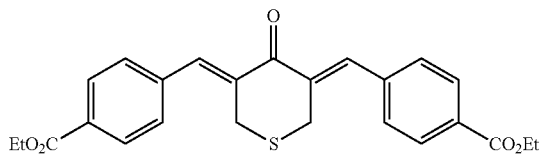 [SMILES: CCOC(=O)c1ccc(/C=C2\CSC/C(=C\c3ccc(C(=O)OCC)cc3)C2=O)cc1]

$^1$H NMR (CDCl$_3$) δ 8.12 (d, J=8.4 Hz, 4H), 7.81 (s, 2H), 7.48 (d, J=7.8 Hz, 4H), 4.42 (q, J=5.4 Hz, 2H), 3.86 (s, 4H), 1.44 (t, J=6.6 Hz, 6H); $^{13}$C NMR δ 188.6, 166.0, 139.4, 135.9, 135.2, 130.7, 129.8, 61.2, 30.0, 14.3; mp 212-215° C.; IR 1582.00, 1602.69, 1663.08, 1682.73, 1712.71; MS (C$_{25}$H$_{24}$O$_5$S) calcd. 436.134 found (M+H) 437.3.

Preparation of 3,5-bis[(3,4-dimethyl-4-methoxyphenyl)methylene]-tetrahydrothiopyran-4-one (7b) Turmerax 7

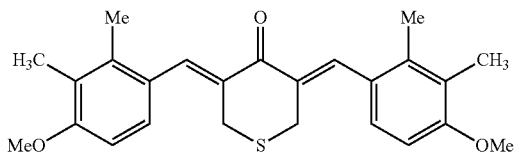 [SMILES: COc1ccc(/C=C2\CSC/C(=C\c3ccc(OC)c(C)c3C)C2=O)c(C)c1C]

$^1$H NMR (CDCl$_3$) δ 7.93 (s, 2H), 7.50 (d, J=8.4 Hz, 2H), 6.76 (d, J=9.0 Hz, 2H), 3.88 (s, 6H), 3.77 (s, 4H), 2.29 (s, 6H), 2.22 (s, 6H); $^{13}$C NMR δ 189.3, 158.0, 137.8, 137.3, 127.4, 127.1, 125.8, 107.2, 55.5, 30.3, 16.8, 11.8; mp 220-222° C.; IR 1478.79, 1583.19, 1651.82, 1662.95; MS (C$_{25}$H$_{25}$O$_5$S) calcd. 408.176 found (M+H) 409.4.

Preparation of 3,5-bis[(2,6-difluoro-3-chlorophenyl)methylene]-tetrahydrothiopyran-4-one (8b) Turmerax 8

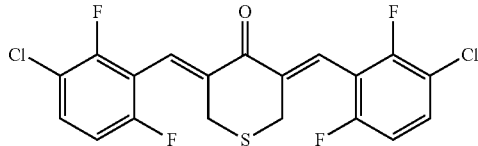 [SMILES: O=C1/C(=C/c2c(F)ccc(Cl)c2F)CSC/C1=C\c1c(F)ccc(Cl)c1F]

$^1$H NMR (CDCl$_3$) δ 7.53 (s, 2H), 7.42 (m, 2H), 6.95 (t, J=8.4 Hz, 2H), 3.59 (s, 4H); $^{13}$C NMR δ 186.3, 138.6, 131.1, 131.0, 123.2, 112.4, 112.3, 112.2, 112.231.06; mp 198-200° C.; IR 1596.01, 1621.36, 1673.83; MS (C$_{19}$H$_{10}$Cl$_2$F$_4$OS) calcd. 431.977 found (M−H) 431.0.

Preparation of 3,5-bis[4-cyanophenyl)methylene]-tetrahydrothiopyran-4-one (9b) Turmerax 9

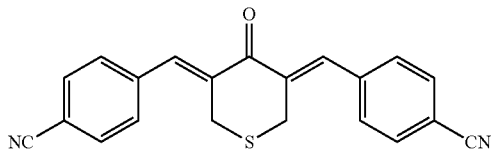 [SMILES: N#Cc1ccc(/C=C2\CSC/C(=C\c3ccc(C#N)cc3)C2=O)cc1]

$^1$H NMR (CDCl$_3$) δ 7.73 (d, J=8.4 Hz, 6H), 7.48 (d, J=7.8 Hz, 4H), 3.86 (s, 4H); $^{13}$C NMR δ 188.1, 139.5, 135.8, 134.9, 132.4, 130.3, 118.3, 112.6, 29.9; mp 228-230° C.; IR 1505.83, 1603.45, 1615.05, 1628.54, 1679.25; MS (C$_{21}$H$_{14}$N$_2$OS) calcd. 342.083 found (M−H) 341.2.

Preparation of 3,5-bis[(4-bromophenyl)methylene]-tetrahydrothiopyran-4-one (10b) Turmerax

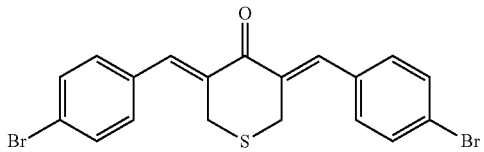 [SMILES: O=C1/C(=C/c2ccc(Br)cc2)CSC/C1=C\c1ccc(Br)cc1]

$^1$H NMR (CDCl$_3$) δ 7.68 (s, 2H), 7.55 (d, J=8.4 Hz, 4H), 7.25 (d, J=8.4 Hz, 4H), 3.86 (s, 4H); $^{13}$C NMR δ 188.6, 135.7, 134.3, 133.9, 131.9, 131.5, 123.4, 30.0; mp 152-154° C.; IR 1577.12, 1600.62, 1661.97; MS (C$_{19}$H$_{14}$Br$_2$OS) calcd. 447.913 found (M−H) 449.3.

Preparation and Incorporation of Turmerax into Liposomes.
Liposomal Preparation

Liposomes are prepared according to previously described methods. A 9:1 ratio of lipids 1,2-dimyristoyl-sn-glycero-3-phosphocholine and 1,2-dimyristoyl-sn-glycerol-3-phospho-rac-(1-glycerol) (i.e. DMPC:DMPG at 9:1 ratio; both from Sigma-Aldrich) is dissolved in tert-butanol at a concentration of 10 mg/mL. Sterile water (1/20 volume) was added and one part Turmerax (purity 99%) was added for a final lipid/Turmerax ratio of 10:1. The solution was sterile-filtered, frozen in dry ice and acetone, and lyophilized overnight. Different total lipid to Turmerax ratios (w/w) ranging from 10:1 to 4:1 were tested before settling on a fixed ratio of 10:1 based on tests to determine optimal encapsulation of Turmerax by liposomes. The lipids and Turmerax were dissolved in tert butanol and filtered through a 0.22-A pore size filter for sterilization. The vials containing lipids and Turmerax (10:1 ratio) solution were frozen in a dry ice-acetone bath and lyophilized for 24 h to remove the tert-butanol. The vials were stored at −20$^C$ C. and warmed to room temperature before use.

Biology:

Effect of Turmerax Compounds in Aggressive Non-Hodgkin's Lymphoma B Cells (NHL-B)

Malignant lymphoma continues to represent a major health issue in the US and worldwide. Non-Hodgkin lymphomas (NHL) are a common, heterogeneous group of primarily (~85%) B lymphoid cell neoplasms (NHL-B) arising in the B cell lineage of the human immune (lymphoid) system. NHL-Bs are the fifth most common cancer in the USA (~65,000 new cases/25,000 deaths expected in 2010). Therefore, there is a great need for novel treatment strategies for this deadly cancer, particularly for relapsed/refractory lymphomas. Relapsed/refractory (r/rDLBCL) DLBCL is one of the most difficult scientific challenges and severe unmet therapeutic needs in clinical oncology today. This is due largely to very drug resistant tumor cells with very poor responses (<20% PR/CR) to current "salvage" therapies. Key pathways (NF-kB, AKT, STAT3), controlling cell growth/survival and chemoresistance in DLBCL have been discovered. Since natural compounds such as turmeric can target multiple pathways with low cellular toxicity, novel compounds with higher potency for cancer cells were sought. Initially, 6 novel turmeric analogues were designed and synthesized using cyclic thioketone and different substituted aromatic aldehydes. These newly synthesized compounds have cell growth inhibition properties in two representative lymphoma cell lines, with IC$_{50}$ values between 2-25 μM (FIG. 1). The most potent compound was selected and 10 additional analogues were synthesized from this compound. These compounds were named turmerax (TMX) (1-10), and tested them in the two resistant mantle cell lymphoma cell lines (Mino and Z-138). 4 out of 10 Turmerax compounds (1, 3, 5, and 9) were discovered to be highly effective growth inhibitors in vitro with IC$_{50}$'s below 1 μM, while 3 out of 10 Turmerax compounds. (2, 6 and 10) showed moderate responses with IC$_{50}$ ranging from 3 μM-10 μM and 3 out of 10 Turmerax compounds. (4, 7 and 8) were not effective with IC$_{50}$ greater than 25 μM (FIG. 2). Turmerax compounds 1, 3, 5 and 9 were further analyzed at concentrations below 1 μM for cell growth inhibition in vitro. Turmerax compounds 1 and 5 were more effective with IC$_{50}$'s in the 100-200 nM ranges, while Turmerax compounds 3 and 9 had IC$_{50}$'s that were in the 200-800 nM ranges (FIG. 3). Next, the toxicity of these Turmerax compounds (1, 3, 5 and 9) was evaluated in normal human peripheral blood mononuclear cells (PBMC). While Turmerax compounds 5 and 9 show some toxicity to PBMC, Turmerax compounds 1 and 3 had only minimal cell toxicity at drug concentration below 600 nM (FIG. 4). The effectiveness of Turmerax compounds 1 and 5 in four MCL cell lines were examined, four LBCL cell lines (both ABC and GCB-type) and one follicular lymphoma cell line (CJ) in comparison to the wild type (natural) curcumin compound, to which these compounds bear some structural relatedness. The IC$_{50}$ for Turmerax cmpds. 1 and 5 were significantly lower (50-150-fold) than the IC$_{50}$ of the wild type curcumin (FIG. 5). Turmerax compounds were more effective in ABC-type DLBCL than the GCB-type, possibly due to higher NF-kB activation in ABC- than in GCB-type DLBCL. The predicted crystal structure model shows that TMX-1 can potentially covalently bind to the NF-kB heterodimer p50/p65 complex and inhibit NF-kB activity (FIG. 6). In fact, TMX-1 potently inhibited NF-kB activity in vitro (FIG. 7, top left) and also targeted multiple growth and survival signaling pathways, such as NIK and AKT (FIG. 7, top right), and can also target chemoresistance DLBCL cells (FIG. 7, bottom). These preliminary results suggest that the turmeric derivative TMX-1 is a potential therapeutic agent for NHL-B cells, that may show effectiveness for relapsed/refractory aggressive NHL-Bs (MCL, DLBCL) that currently lack effective therapeutic agents.

Figure 8:
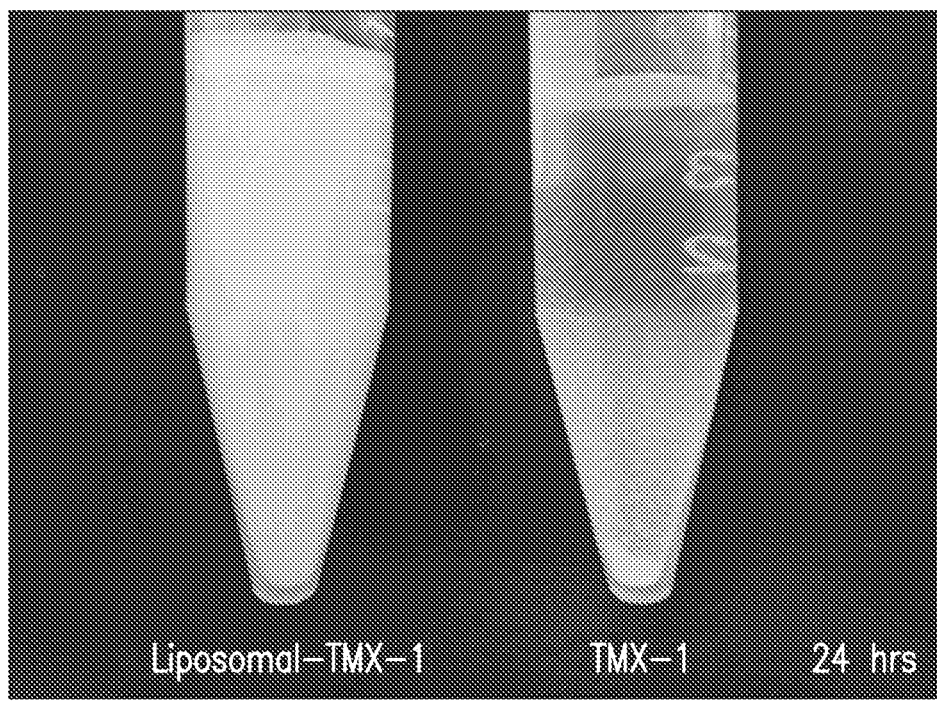
FIG. 8. Water Solubility of Lipo-Turmerax-1 Compound. Liposomal TMX-1 and TMX-1 compounds were suspended in water for 24 hrs. Non-liposomal TMX-1 compound shows precipitation, while liposomal formulation did not.

Although TMX-1 displayed a reduced bio-availability, for example in vivo, the solubility/bio-availability was significantly improved by using an efficient liposomal nanocarrier as a nanocarrier formulation for drug delivery of TMX-1. The solubility of Lipo-TMX-1 in water is much higher than TMX-1 alone (FIG. 8). When encapsulated with nano-liposomes to improve solubility/bioavailability, Turmerax is >1000× more effective than natural curcumin or other type of nanoformulation (PbAE, poly(beta-amino ester) in inhibiting DLBCL growth in vitro (FIG. 9). The results also show that in vivo L-TMX increases in survival time with decreases in lymphoma tumor burden in preliminary studies in SCID/MCL xeno-transplant (XT-SCID) models, without evidence of significant host toxicities (FIG. 10). The development of nano-liposomal Turmerax, can be used as a multi-targeted, non-toxic nano-therapeutic small molecule with the critical growth/survival (G/S) targeting specificities similar to natural product therapeutic agents (curcumin) but without the many foibles involving solubility, bioavailability, and poor in vivo potency problems, by providing a well-tolerated, well-delivered (in vivo) effective small molecule therapeutic agent, showing very promising preliminary activities on r/r DLBCL and MCL in xeno-transplant SCID mouse models. These formulations may be used in further clinical trials. Experiments also indicated that TMX-1 is highly effective in inhibiting solid tumor cancer cells, such as melanoma, gastric, pancreatic, and glioma (FIG. 11).

Example 2

Understanding the Mechanisms of Action of TMX-1.

The above results indicate that TMX-1 is highly effective in inhibiting lymphoma cell growth, but its mechanism of action is still unclear. To determine whether TMX-1 can induce apoptosis in lymphoma cells, we treated a diffuse large cell lymphoma (DLBCL) cell line (LY-10) with TMX-1 in a dose-dependent manner for 24 hrs. Control and treated cells were analyzed for apoptosis using Annexin V assays. The results showed that TMX-1 is highly effective (up to 80% at 500 nM drug concentration) in inducing apoptosis in LY10 cells (FIG. 12A). Next, we test whether TMX-1 can induces DNA damage in LY-10 cells. As shown in FIG. 12B, the marker for DNA damage, pH2AX, was significantly increased in TMX-1 treated cells. In addition, the anti-apoptotic protein bcl-2 was cleaved after TMX-1 treatment in LY-10 cells, suggesting one potential mechanism of TMX-1 inducing apoptosis in LY-10 cells is through the intrinsic mitochondria pathway. The inventors also examined whether TMX-1 can inhibit NF-kB activity in lymphoma cells. For these studies, a DLBCL cell line (MS) was transfected with a NF-kB luciferase reporter for 24 hrs, at which time cells were treated with TMX-1 in a dose- and time-dependent manner. The results showed that TMX-1 can inhibit NF-kB activity as early as 1 hr after treatment. Without wishing to be bound by any theory, these results support the idea that the dynamic on this agent on NF-kB inhibition could in the nucleus through direct interaction with DNA. There are many NF-kB inhibitors commercially available that have been tested in many cancer systems, but none has ever reached the clinic to cancer treatment. The reason for this is typically because these agents usually target upstream of NF-kB signaling pathways, leading to many unwanted side effects. These results support the idea that TMX-1 may be the first-in-class compound to target NF-kB through direct interaction with DNA.

Reversing Chemoresistance in DLBCL with TMX-1.

Figure 13A:
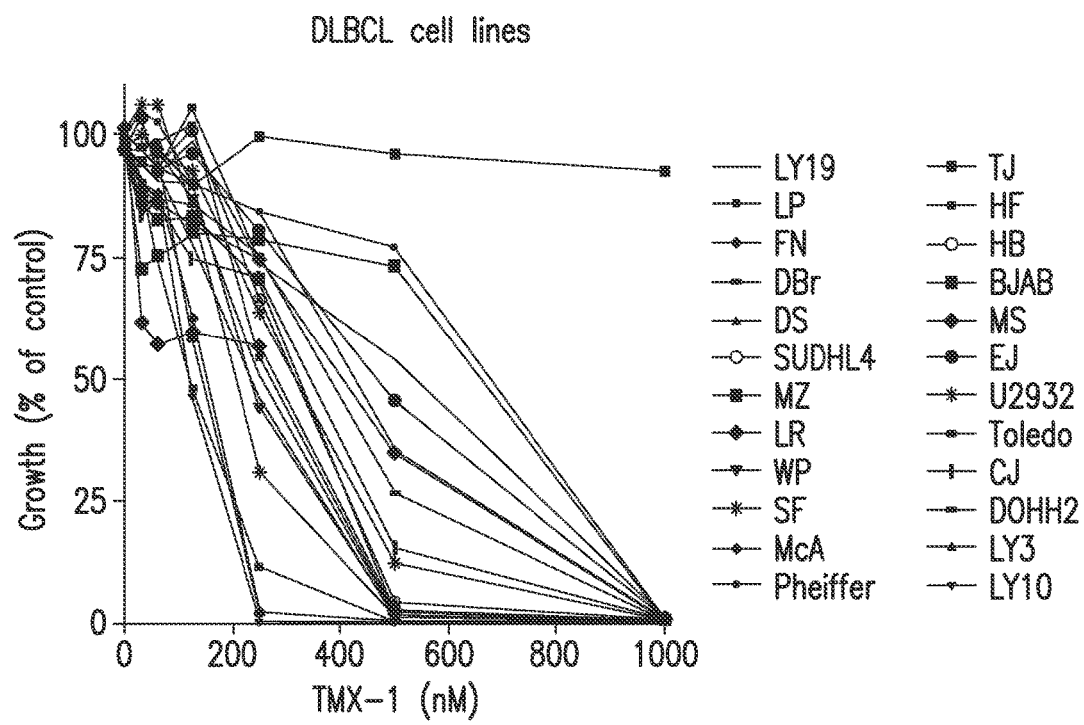
FIGS. 13A-B. TMX-1 inhibits DLBCL cell proliferation.
Figure 13B:
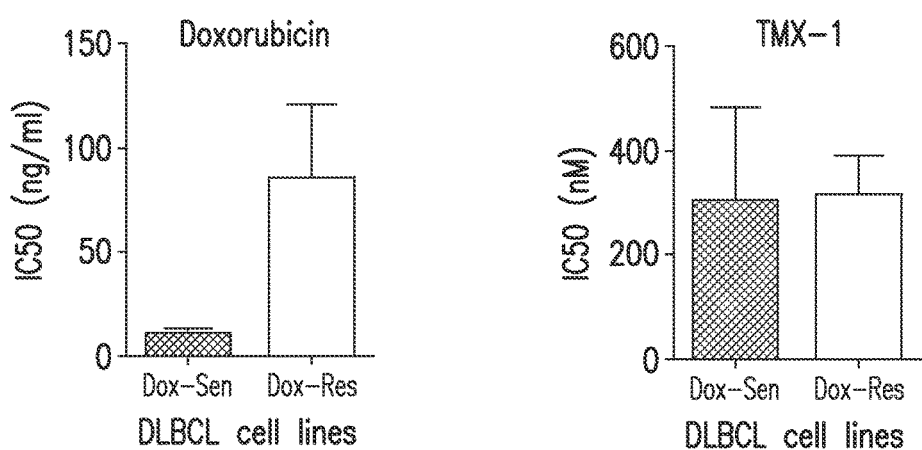

DLBCL are currently initially treated fairly successfully with R-CHOP frontline chemotherapy (~70-80% initial remission rate), but relapsed/refractory DLBCL occurs frequently (~40% within 2-3 yrs), with very poor salvage therapy options (~20% PR/CR). A unique repertoire of human DLBCL cell lines were developed (Ford et al., 1990; Pham et al., 2010) that can be classified into two subgroups, doxorubicin (a key component in CHOP)-sensitive and doxorubicin-resistant. These cell lines were screened against TMX-1 in a dose-dependent manner using 72-hr proliferation assays (FIG. 13A). TMX-1 activity is equivalent in Dox-sensitive vs. Dox-resistant DLBCL cell lines (FIG. 13B), suggesting that TMX-1 is capable of reversing chemoresistant in DLBCL.

TMX-1 in Combination with Targeted Therapeutic Agents to Treat DLBCL.

Recent molecularly targeted therapy, as opposed to classic chemotherapy, has improved the treatment of lymphoid malignancies. At the forefront of clinical development are ibrutinib, an inhibitor of Bruton's tyrosine kinase (btk) and carfilzomib (CFZ), a second-generation proteasome inhibitor. Our initial studies indicated that TMX-1 in combination with ibrutinib was more effective than TMX-1 in combination with CFZ (FIG. 14A). Further experiments confirmed that TMX-1 is highly synergistic with ibrutinib to inhibit lymphoma cell growth (FIG. 14B).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos. 5,641,515; 5,580,579 and 5,792, 451
U.S. Pat. No. 5,629,001
U.S. Pat. Nos. 6,613,308, 5,466,468, 5,543,158; 5,641,515; and 5,399,363
U.S. Pat. No. 5,466,468
U.S. Pat. Nos. 5,756,353 and 5,804,212

U.S. Pat. No. 5,725,871
U.S. Pat. No. 5,780,045
Anderson, N. G., *Practical Process Research & Development—A Guide For Organic Chemists*, 2nd ed., Academic Press, New York, 2012.
*Handbook of Pharmaceutical Salts: Properties, and Use*, Stahl and Wermuth Eds.), Verlag Helvetica Chimica Acta, 2002.
*March's Advanced Organic Chemistry: Reactions*, Mechanisms, and Structure, 2007.
*Remington: The Science and Practice of Pharmacy*, 21st Ed. Lippincott Williams and Wilkins, 2005
Remington's Pharmaceutical Sciences, 15th ed., pages 1035-1038 and 1570-1580, Mack Publishing Company, Easton, Pa., 1980.
Remington's Pharmaceutical Sciences, 18th Ed. Mack Printing Company, 1289-1329, 1990.
Mathiowitz et al., *Nature*, 386(6623):410-414, 1997.
Hwang et al., *Crit. Rev. Ther. Drug Carrier Syst.*, 15(3): 243-284, 1998.
Pham et al., Blood, November 2011; 118:1428.
Ford et al., Blood; 75(6):1311-8.
Pham et al., Blood; 116(19):3899-906.

The invention claimed is:

1. A pharmaceutical preparation comprising a compound having the structure:

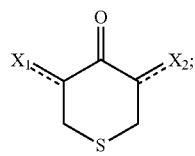

wherein $X_1$ is —H or

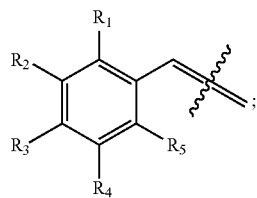

wherein $X_2$ is —H or

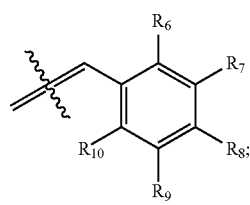

wherein $X_1$ and $X_2$ are not both —H;
wherein $R_1$, $R_2$, $R_3$, $R_4$, $R_5$, $R_6$, $R_7$, $R_8$, $R_9$, and $R_{10}$ are each independently —H, —OH, halogen, alkoxy$_{(C1-6)}$, alkylamino$_{(C1-6)}$, dialkylamino$_{(C1-6)}$, acyl$_{(C1-7)}$, alkyl$_{(C1-6)}$, —NH$_2$, —NO$_2$, —CO$_2$H, —CO$_2$-alkyl$_{(C1-6)}$, —CN, —SH, —C(O)NH$_2$, —OC(O)CH$_3$, or —S(O)$_2$NH$_2$; wherein $R_1$-$R_{10}$ are not all hydrogen; or a salt thereof;
wherein the compound is comprised in the pharmaceutical preparation.

2. The pharmaceutical preparation of claim 1, wherein the compound has the structure:

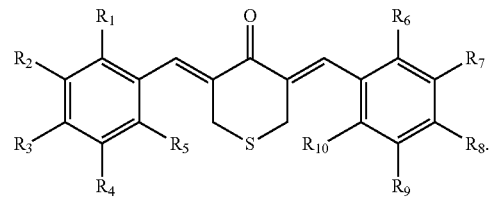

3. The compound pharmaceutical preparation of claim 2, wherein $R_1$, $R_2$, $R_3$, $R_4$, $R_5$, $R_6$, $R_7$, $R_8$, $R_9$, and $R_{10}$ are each independently —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —CH$_3$, —CH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

4. The pharmaceutical preparation of claim 3, wherein $R_1$, $R_2$, $R_3$, $R_4$, $R_5$, $R_6$, $R_7$, $R_8$, $R_9$, and $R_{10}$ are each independently —H, —OH, —F, —Cl, —Br, —I, —NO$_2$, —CN, —SH, —OCH$_3$, or —OCH$_2$CH$_3$.

5. The pharmaceutical preparation of claim 4, wherein $R_1$, $R_2$, $R_3$, $R_4$, $R_5$, $R_6$, $R_7$, $R_8$, $R_9$, and $R_{10}$ are each independently —H, —OH, —F, —Cl, —Br, —I, —NO$_2$, or —CN.

6. The pharmaceutical preparation of claim 2, wherein $R_1$, $R_2$, $R_3$, $R_4$, $R_5$, $R_6$, $R_7$, $R_8$, $R_9$, and $R_{10}$ are alkoxy$_{(C1-6)}$, dialkylamino$_{(C1-6)}$, acyl$_{(C1-7)}$, or alkyl$_{(C1-6)}$.

7. The pharmaceutical preparation of claim 2, wherein the compound is further defined as having the structure:

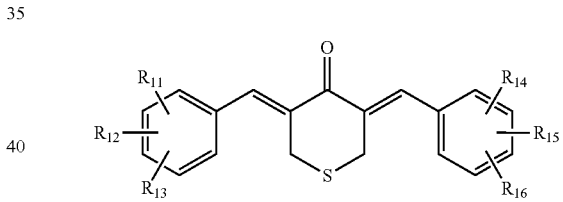

wherein $R_{11}$, $R_{12}$, $R_{13}$, $R_{14}$, $R_{15}$, and $R_{16}$ are each independently —H, —OH, halogen, alkoxy$_{(C1-6)}$, alkylamino$_{(C1-6)}$, dialkylamino$_{(C1-6)}$, acyl$_{(C1-7)}$, alkyl$_{(C1-6)}$, —NH$_2$, —NO$_2$, —CO$_2$H, —CO$_2$CH$_3$, —CN, —SH, —C(O)NH$_2$, —OC(O)CH$_3$, or —S(O)$_2$NH$_2$.

8. The pharmaceutical preparation of claim 7, wherein $R_{11}$, $R_{12}$, $R_{13}$, $R_{14}$, $R_{15}$, and $R_{16}$ are each independently —H, —OH, —NO$_2$, —CN, —F, —Cl, —Br, —I, —OCH$_3$, —OCH$_2$CH$_3$, —C(O)OCH$_3$, —C(O)OCH$_2$CH$_3$, —CH$_3$, or —CH$_2$CH$_3$.

9. The pharmaceutical preparation of claim 7, wherein the compound is further defined as having the structure:

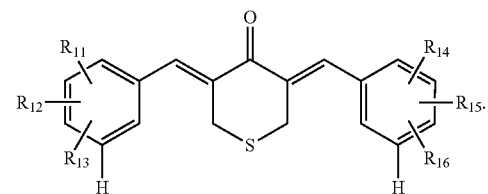

10. The pharmaceutical preparation of claim 2, wherein $R_1$, $R_4$, $R_5$, $R_6$, $R_9$, and $R_{10}$ are —H.

11. The pharmaceutical preparation of claim 10, wherein $R_2$ and $R_7$ have the same substituent, or $R_3$ and $R_8$ have the same substituent.

12. The pharmaceutical preparation of claim 11, wherein $R_2$ and $R_7$ have the same substituent, and wherein $R_3$ and $R_8$ have the same substituent.

13. The pharmaceutical preparation of claim 10, wherein $R_2$, $R_3$, $R_7$, and $R_8$ are each independently —H, —OH, halogen, alkoxy$_{(C1-6)}$, alkylamino$_{(C1-6)}$, dialkylamino$_{(C1-6)}$, acyl$_{(C1-7)}$, alkyl$_{(C1-6)}$, —NH$_2$, —NO$_2$, —CO$_2$H, —CO$_2$-alkyl$_{(C1-6)}$, —CN, —SH, —C(O)NH$_2$, —OC(O)CH$_3$, or —S(O)$_2$NH$_2$.

14. The pharmaceutical preparation of claim 13, wherein $R_2$, $R_3$, $R_7$, and $R_8$ are each independently —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —CH$_3$, —CH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

15. The pharmaceutical preparation of claim 14, wherein $R_2$, $R_3$, $R_7$, and $R_8$ are each independently —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

16. The pharmaceutical preparation of claim 15, wherein $R_2$, $R_3$, $R_7$, and $R_8$ are each independently —H, —OH, —Cl, —Br, —NO$_2$, or —CN.

17. The pharmaceutical preparation of claim 16, wherein $R_2$ and $R_7$ are —OH, —Cl, —Br, —NO$_2$, or —CN.

18. The pharmaceutical preparation of claim 16, wherein $R_3$ and $R_8$ are —OH, —Cl, —Br, —NO$_2$, or —CN.

19. The pharmaceutical preparation of claim 1, wherein the compound has the structure:

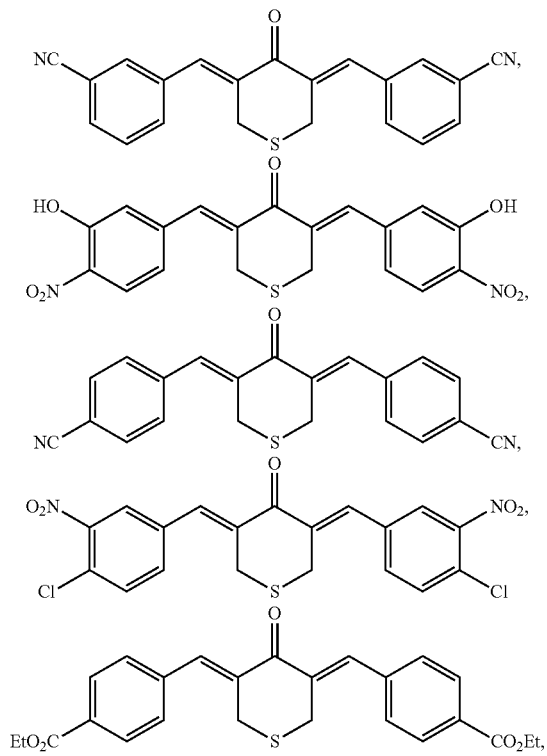

20. The pharmaceutical preparation of claim 19, wherein the compound has the structure:

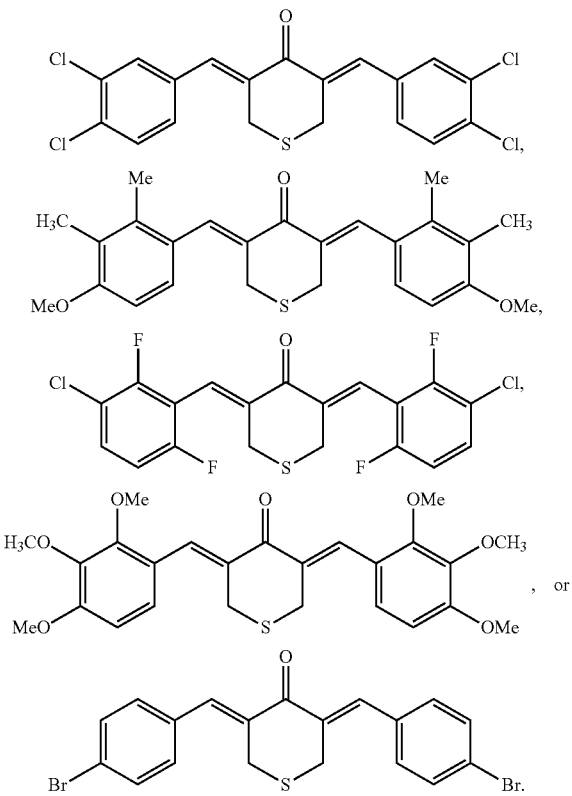
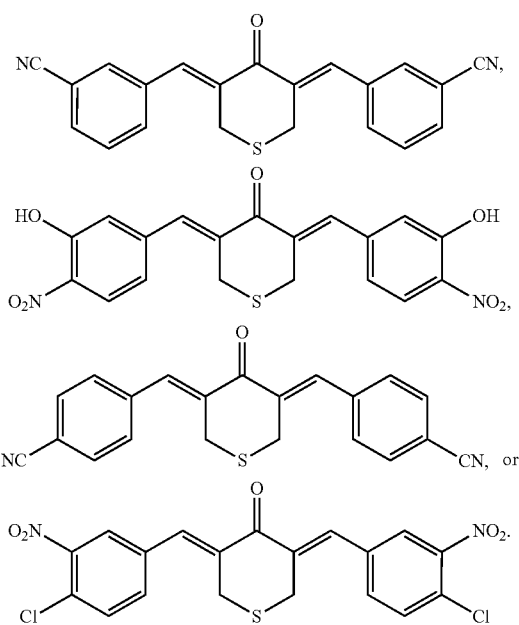

21. The pharmaceutical preparation of claim 1, wherein the compound has the structure:

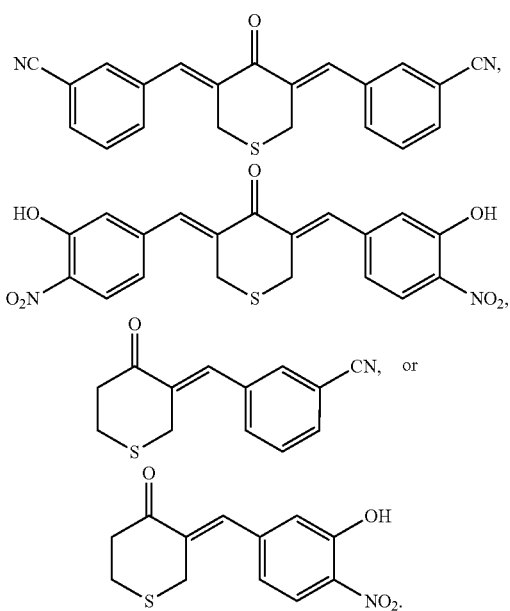

22. The pharmaceutical preparation of claim 1, wherein the pharmaceutical preparation is formulated for oral, intravenous, intratumoral, subcutaneous, intraperitoneal, or parenteral administration.

23. The pharmaceutical preparation of claim 1, wherein the compound is comprised in a nanoparticle, an exosome, a lipid formulation, or a liposome formulation.

24. The pharmaceutical preparation of claim 23, wherein the compound is comprised in a lipid formulation, wherein the lipid is an oil or sesame oil.

25. The pharmaceutical preparation of claim 23, wherein the compound is comprised in a liposome formulation, wherein the liposome comprises N-[1-(2,3-Dioleoyloxy) propyl]-N,N,N-trimethylammonium methyl-sulfate (DOTAP), Lipofectamine™, 1,2-dimyristoyl-sn-glycero-3-phosphocholine (DMPC), or 1,2-dimyristoyl-sn-glycero-3-phospho-rac-(1-glycerol) (DMPG).

26. The pharmaceutical preparation of claim 25, wherein the liposome comprises 1,2-dimyristoyl-sn-glycero-3-phosphocholine (DMPC) and 1,2-dimyristoyl-sn-glycero-3-phospho-rac-(1-glycerol) (DMPG).

27. The pharmaceutical preparation of claim 26, wherein the liposome comprises a ratio of 1,2-dimyristoyl-sn-glycero-3-phosphocholine (DMPC) to 1,2-dimyristoyl-sn-glycero-3-phospho-rac-(1-glycerol) (DMPG) of about 9:1.

28. The pharmaceutical preparation of claim 25, wherein the liposome comprises a ratio of N-[1-(2,3-Dioleoyloxy) propyl]-N,N,N-trimethylammonium methyl-sulfate (DOTAP), Lipofectamine™, 1,2-dimyristoyl-sn-glycero-3-phosphocholine (DMPC), or 1,2-dimyristoyl-sn-glycero-3-phospho-rac-(1-glycerol) (DMPG) to the compound from about 4:1 to about 10:1.

29. The pharmaceutical preparation of claim 28, wherein the ratio of N-[1-(2,3-Dioleoyloxy)propyl]-N,N,N-trimethylammonium methyl-sulfate (DOTAP), Lipofectamine™, 1,2-dimyristoyl-sn-glycero-3-phosphocholine (DMPC), or 1,2-dimyristoyl-sn-glycero-3-phospho-rac-(1-glycerol) (DMPG) to the compound is about 10:1.

30. A method of treating, preventing, or reducing the likelihood of a cancer in a subject comprising administering a pharmaceutically effective amount of the pharmaceutical preparation of claim 1 to treat the cancer.

31. A method of treating inflammation in a subject comprising administering a pharmaceutically effective amount of the pharmaceutical preparation of claim 1 to treat the inflammation.

32. A method of treating an angiogenic disease or reducing angiogenesis in a subject comprising administering a pharmaceutically effective amount of the pharmaceutical preparation of claim 1 to reduce angiogenesis.

* * * * *

UNITED STATES PATENT AND TRADEMARK OFFICE
CERTIFICATE OF CORRECTION

PATENT NO. : 10,208,012 B2
APPLICATION NO. : 14/774620
DATED : February 19, 2019
INVENTOR(S) : Richard J. Ford, Jr. et al.

Page 1 of 1

It is certified that error appears in the above-identified patent and that said Letters Patent is hereby corrected as shown below:

In the Claims

In Claim 3, Column 40, Line 14, delete "compound".

In Claim 6, Column 40, Line 30, after "alkoxy$_{(C1-C6)}$," insert --alkylamino$_{(C1-C6)}$,--.

Signed and Sealed this
Twenty-eighth Day of May, 2019

Andrei Iancu
*Director of the United States Patent and Trademark Office*